(12) United States Patent
Lee et al.

(10) Patent No.: US 7,662,915 B2
(45) Date of Patent: Feb. 16, 2010

(54) PEPTIDES HAVING PROTECTED AMINES OF UNTARGETED SITES, METHODS FOR PRODUCTION THEREOF AND OF SPECIFICALLY CONJUGATED PEG PEPTIDES USING THE SAME

(75) Inventors: Sang Deuk Lee, Seoul (KR); Kang Choon Lee, Seoul (KR); Dong Hee Na, Seoul (KR); Yu Seok Youn, Seoul (KR)

(73) Assignee: Pegsphere Co., Ltd., Suwon (KR)

( * ) Notice: Subject to any disclaimer, the term of this patent is extended or adjusted under 35 U.S.C. 154(b) by 322 days.

(21) Appl. No.: 10/542,230

(22) PCT Filed: Jan. 18, 2003

(86) PCT No.: PCT/KR03/00118

§ 371 (c)(1),
(2), (4) Date: Jul. 15, 2005

(87) PCT Pub. No.: WO2004/065412

PCT Pub. Date: Aug. 5, 2004

(65) Prior Publication Data

US 2006/0063914 A1   Mar. 23, 2006

(51) Int. Cl.
  *C07K 1/06* (2006.01)
  *C07K 1/107* (2006.01)
  *C07K 1/04* (2006.01)
  *C07K 1/00* (2006.01)

(52) U.S. Cl. ........................ 530/335; 530/333; 530/334; 530/339

(58) Field of Classification Search .................. None
See application file for complete search history.

(56) References Cited

U.S. PATENT DOCUMENTS 6,528,485 B1 *  3/2003  Veronese et al. .............. 514/12

FOREIGN PATENT DOCUMENTS

EP           922446 A1 *  6/1999

OTHER PUBLICATIONS

T. Shi and D.L. Rabenstein. Bioorg. Med. Chem. Letters (2002) 12(16), pp. 2237-2240.*
F. Alberecio. Biopolymers (2000) 55, pp. 123-139.*
D. Kadereit et al. Chem. Eur. J. (2001) 7(6), pp. 1184-1193.*
K. Barlos and M. Gatos. Biopolymers (1999) 51, pp. 266-278.*
J. Wilken and S.B.H. Kent. Curr. Opinion Biotech. (1998) 9, pp. 412-426.*
Lee et al., "Site-specific PEGylated Peptide Drugs for Enhanced Therapeutic Efficacy," Presentation, Controlled Release Society 29th Annual Meeting Proceedings, Jul. 20-25, 2002, 2 pps.
Lee et al., "Preparation of Site-specific PEGylated Growth Hormone-Releasing Factor 1-29," Presentation, American Association of Pharmaceutical Scientists, Annual Meeting, Nov. 11, 2002 (Abstract only) (2 pps.).

* cited by examiner

*Primary Examiner*—Andrew D Kosar
(74) *Attorney, Agent, or Firm*—Heslin Rothenberg Farley & Mesiti P.C.

(57) ABSTRACT

The present invention relates to synthetic peptides having selectively protected amines of untargeted sites and to methods for production thereof and for specifically conjugating PEG to targeted sites of the synthetic peptides using the same. The present invention provides a much higher yield of PEG conjugated peptides in which PEG is specifically combined to amines at targeted sites.

7 Claims, 6 Drawing Sheets

PEPTIDES HAVING PROTECTED AMINES OF UNTARGETED SITES, METHODS FOR PRODUCTION THEREOF AND OF SPECIFICALLY CONJUGATED PEG PEPTIDES USING THE SAME

CROSS REFERENCE TO RELATED APPLICATIONS

This application is a 371 filing of PCT International application no. PCT/KR2003/000118 filed Jan. 18, 2003 and published in English as WO 2004/065412 on Aug. 5, 2004, the disclosure of which is hereby incorporated by reference in its entirety.

TECHNICAL FIELD

The present invention relates to methods of specifically conjugating at least one PEG(polyethylene glycol)s to amines of targeted sites in synthetic peptide with at least two branched amines, and further relates to synthetic peptides having selectively protected amines of untargeted sites and methods for the production thereof, and to method of specifically conjugating PEGs to targeted sites of the synthetic peptide and purifying by ion exchange chromatography.

BACKGROUND ART

Technologies for conjugating PEG to peptides and proteins are based on Davis and Abuchowski study (Abuchowski A. et al., *J. Biol. Chem.*, 252, 3571-3581, 1977; Abuchowski A. et al., *J. Biol. Chem.*, 252, 3582-3586, 1977). PEG is a polymer which is hydrophilic, biocompatible and harmless having the structure of $H(OCH_2CH_2)_nOH$ and it is known that in case of being conjugated to peptide and protein, it inhibits enzymatic metabolism via steric hindrance as the same way as sugar chain in glycoprotein does, decreases renal glomerular filtration with increased molecular size of peptide and protein having conjugated PEGs, thereby increasing the duration of physiological activity. Covalent bond between polypeptide and PEG was published in U.S. Pat. No. 4,179,337, and it was described that modification of proteins and enzymes with PEG leads to reduced immunogenicity and antigenicity and increased half life within blood.

For covalent bonding of PEG to polypeptide, it is necessary that "activation" process of converting the terminal hydroxyl moiety of PEG to a reactive functional group. As an "activated PEG", alkylating agents such as PEG aldehydes, PEG epoxides and PEG tresylates, and acylating agents such as PEG esters can be enumerated, and the representative example is PEG succinimidyl succinate. Poly(ethyleneglycol)-N-succinimide carbonate and producing method thereof was known from Abuchowski et al., *Cancer Biochem. Biophys.* 7:175-186(1984) and U.S. Pat. No. 512,614 etc. PEGs in molecular range of 2,000-40,000 can be employed and PEGs such as methoxylated PEGs and branched PEGs can be used. The branched PEG can be represented with the structure of $R(-PEG-OH)_m$ [herein, R defines central core moiety such as pentaerythritol or glycerol, m defines the number of branching arm in a range of 3-100]. Hydroxyl group can be used for chemical modification. Other branched PEG with the structure of $(CH_3O-PEG-)_pR$—X (WO96/21469) is employed [herein, p is 2 to 3, R represents central core moiety such as lysine and glycerol, and X defines a functional group such as carboxyl group used for activation. Pendant PEG of another branched PEG has functional group such as carboxyl moiety on PEG backbone, other than terminus of PEG chain. All these branched PEGs can be used via "activation" as described previously.

In the reaction of conjugating "activated" PEGs to peptide amines, generally, PEGs bond to one or more amines nonspecifically, thus the core of this technology lies in the method of specifically combining PEG molecules to amines at specific positions. However, in case of peptides containing at least one lysine within the amino acid sequence, as two or more amines exist therein, it is very difficult to specifically conjugate PEGs to amines at specific sites. In case PEGs are conjugated to peptide according to general methods, various conjugates can be generated, from a conjugate having one conjugated PEG to a conjugate having multiple-conjugated PEGs as many as the number of amines, and even in case of the conjugate having one PEG (a mono-PEG conjugate), positional isomers in which conjugation sites of PEG are different one another, can be formed. Usually, as PEG conjugates of peptide differ in activity and enzymatic metabolism according to the number of combined PEGs and combined sites thereof, the method producing such mixture containing various conjugates is disadvantageous for the reason of very low activity yield and being a mixture. To separate and purify specific isomer from the mixture is very complicated, accompanied by very low yield and high cost. To compensate such disadvantages, various methods for site-specific PEGylation have been proposed, however, efficient methods for specific conjugation of PEGs to amines on specific positions has not yet been developed.

*Chem. Pharm. Bull.* 39(12): 3373-3375(1991) reported on a conjugate of fibronectin-related tripeptide(Arg-Gly-Asp) and amino-poly(ethyleneglycol) and activity thereof. Herein, a method for preparing PEG conjugate by combining amino PEG to aspartic acid activated with dicyclohexylcarbodiimide(DCC)/1-hydroxybenzotriazole(HOBt), was proposed. However, this method is defective in that it can be used only for modification of C-terminus and racemization of adjacent amino acids can occur during the C-terminal activation of peptide. Such racemization can occur in every amino acids except glycine, resulting in reduction of activity of peptide.

Methods for combining monomethoxy poly(ethyleneglycol)(mPEG) or polyvinylalcohol(PVA) to peptide using synthetic resin were published in *Journal of Protein Chemistry* 10(6):623-627(1991). Since only the conjugate in which a single polymer is combined to N-terminus of the peptide from the method, it fails to provide a method for combining PEG to positions that can maximize the effect of PEGylation (maximizing the duration of peptide activity and minimizing enzymatic metabolism).

PCT patent application No. PCT/US94/06953(1994) provides methods for preparing site-specific PEG peptide in which PEG is introduced during synthetic process of the peptide. That is, it provides a method for preparing PEG-conjugated peptide in which peptide is partially synthesized until its sequence reaches lysine at targeted position, and then PEG is combined, and finally the remaining portion of the peptide is synthesized to complete PEG peptide, a method for preparing PEG-conjugated peptide by using, as the lysine of targeted site, lysine in which $N^\alpha$-amine thereof was protected with Fmoc(9-fluorenylmethoxycarbonyl) and branched amine thereof was combined with PEG, and a method wherein peptide fragment having PEGs combined to the amines of targeted sitse and the remaining peptide fragment were separately synthesized and combined to complete the PEG-conjugated peptide. Nevertheless, such methods might bring undesirable result due to the effect of the previously combined PEG on subsequent step of the synthesis. For example, in case PEG is introduced during the peptide synthesis and synthesis of the remaining portion is to be continued, a peptide lacking at least one amino acid of the amino acid sequence might be produced, and such peptide can b harmful to a living body and its purification is almost impossible. Therefore, such method is not desirable as a method for preparing a PEG-conjugated peptide usable as a medicine.

PCT patent application No. PCT/EP98/07748 provides methods for combining PEG to amine of GRF in an organic solvent and purifying the resulting mixture of Lys(PEG)$^{12}$-GRF, Lys(PEG)$^{21}$-GRF, Lys(PEG)$^{12,21}$-GRF and [N$^\alpha$-PEG-Try$^1$, Lys(PEG)$^{12,21}$]-GRF by gel chromatography and reverse phase chromatography. However, this method cannot provide specificity between amine moieties of N$^\alpha$, Lys$^{12}$ and Lys$^{21}$. Said patent also provides methods for synthesis of [Lys(Alloc)$^{12,21}$]-GRF(1-29) and [N$^\alpha$-isopropyl-Try$^1$, Lys(Alloc)$^{12}$]-GRF(1-29) and specific PEGylation using them, though, in case of [Lys(Alloc)$^{12,21}$]-GRF(1-29), PEG can be conjugated to only N$^\alpha$ amine, and fails to provide a preparing method for Lys$^{21}$-PEG conjugate which is most effective as described in said patent. In addition, in case PEG conjugate is prepared by using [N$^\alpha$-isopropyl-Try$^1$, Lys(Alloc)$^{12}$]-GRF (1-29), not PEG conjugate of GRF(1-29)-NH$_2$ but PEG conjugate of [N$^\alpha$-isopropyl-Try$^1$]-GRF(1-29)-NH$_2$, i.e. [N$^\alpha$-isopropyl-Try$^1$, Lys(PEG)$^{21}$]-GRF(1-29) is to be formed. Therefore, this method fails to provide completely specific PEGylation for the original peptide having N-terminal amine, GRF(1-29)-NH$_2$.

The inventors of the present invention intended to develop specific PEGylation by which product yield can be noticeably raised and efforts and cost needed for separation and purification of the final product can be reduced, by forming the final product in which PEGs are conjugated only to amines at targeted sites while preventing the formation of impurity product having PEGs conjugated to amines of untargeted sites.

The present invention provides method for preparing specific PEG-conjugated peptide in which the effect of PEG conjugation is maximized by allowing PEGs to be conjugated to amines at targeted sites only with complete selectivity.

DISCLOSURE OF THE INVENTION

The present invention relates to synthetic peptides having selectively protected amines of untargeted sites, methods for production thereof, and methods for specifically conjugating PEGs to targeted sites of the synthetic peptide. In more detail, the present invention relates to (A) a method for preparing peptides having selectively protected amines of untargeted sites, comprising synthesizing the peptide by separately blocking amines of targeted sites and amines of untargeted sites with different protecting groups which are removed under different deblocking condition {e.g. ivDde[1-(4,4-dimethyl-2,6-dioxocyclohexylidene)-3-methylbutyl] or Mtt(4-methyltrityl), and Boc(tert-buthoxycarbonyl)} and protecting N$^\alpha$-amine with Fmoc or Nsc, (B) peptides having selectively protected amines of untargeted sites prepared by said method and (C) methods for preparing specific PEG-conjugated peptide in which PEG are specifically conjugated to amines of targeted sites, comprising (1) reacting said peptide with activated PEGs and (2) removing the amine blocking groups of the compound obtained in said step (1) under acid-base deblocking conditions.

The present invention further relates to methods for preparing peptides having selectively protected amines of untargeted sites, additionally comprising a step of substituting the protecting groups of the amines at untargeted sites, including N$^\alpha$-amine of the peptide synthesized as described above with final amine protecting groups.

As the final amine protecting groups, at least one selected from the group consisting of Fmoc, Nsc, Dde, ivDde and other protecting groups removed under basic conditions, can be used, or at least one selected from the group consisting of Boc and other protecting groups removed under acidic conditions, can be used.

One of general methods for synthesizing peptide is to repeat the reaction in which carboxyl moiety of C-terminal amino acid with protected N$^\alpha$-amine is combined to resin, deblocking of the amine is conducted under basic condition, and according to the sequence, next amino acid with protected N$^\alpha$-amine is combined, thereby reaching N-terminal amino acid. In case lysine having branched amine is contained in the amino acid sequence, lysine in which the branched amine is protected with Boc removed under acidic condition and N$^\alpha$-amine is protected with Fmoc or Nsc[4-nitrophenylsulfonylethoxycarbonyl] removed under basic condition is used, thereby allowing the branched amine not to undergo deblocking under the deblocking condition of N$^\alpha$-amine for combining subsequent amino acid. However, in case of peptide having at least two branched amines, as distinction between the branched amines is difficult, synthesis of completely selectively protected peptide was difficult. In synthesizing peptides with at least two branched amines, the inventors of the present invention synthesized selectively protected peptide in which the branched amines can be differentiated simply based on acid-base deblocking management by using Fmoc or Nsc as protecting groups of N$^\alpha$-amine and two kinds of amine protecting groups removed under different conditions, i.e. either Boc and ivDde or Mtt as protecting groups of the branched amines, and based on this, developed completely specific PEGylation, thereby completing the present invention. The reason for differentiating between branched amines of untargeted sites and N-terminal amine and using individually different protecting groups is because only N-terminal amine should be selectively reacted upon synthesis of peptide. Amines at untargeted sites may be substituted with other protecting groups at final step of the peptide synthesis according to necessity for stability under PEGylation conditions. As this method enables synthesis of selectively protected peptide simply by modifying acid-base conditions, it is advantageous compared to the methods based on reductive reaction or allyl substitution in that the reaction is simple, economical and yielding the peptide with high purity.

For example, as specific embodiments of the present invention, the following methods can be enumerated.

In case of method in which branched amines of targeted sites are protected with Boc and branched amines of untargeted sites are protected with ivDde, in the step of introducing lysine of targeted site, a lysine in which N$^\alpha$-amine is protected with Fmoc or Nsc and branched amine is protected with Boc is used, and in the step of introducing lysine of other sites, lysine where N$^\alpha$-amine is protected with Fmoc or Nsc and branched amine is protected with ivDde, is used for the peptide synthesis. During the procedure for the synthesis, ivDde is not removed under deblocking condition of Fmoc or Nsc, e.g. 1% DBU(1,8-diazabicyclo[5,4,0]undes-7-ene)-20% piperidine/DMF (N,N-dimethylformamide).In case of the synthesized peptide-resin(branched amine of targeted site is protected with Boc, branched amine of untargeted site, with ivDde, and N-terminal amine, with Fmoc or Nsc), after ivDde on branched amine of untargeted site and Fmoc on N-terminal amine are removed, thus resulting free amine is protected with Fmoc or Nsc {for instance, by reacting with Fmoc-Osu (9-fluorenylmethoxycarbonyl-succinamide) or Nsc-OSu}. At this time, said deblocking can be conducted, for example, by treating with 2% hydrazine solution. This peptide-resin is treated with cleavage solution (for example, triisopropylsilane(TIS):water:trifluoroacetic acid(TFA) =2.5:2.5:95) to separate peptide from resin and at the same time, to remove Boc on amine of targeted site, thereby obtaining peptide in which amines of untargeted site are protected with Fmoc or Nsc.

In case of method in which branched amine of targeted site is protected with Boc and branched amines of untargeted site are protected with Mtt, in the step of introducing lysine of targeted site, lysine in which $N\alpha$- is protected with Fmoc or Nsc and branched amine is protected with Boc is used, and in the step of introducing lysine at other sites, lysine where $N^\alpha$-amine is protected with Fmoc or Nsc and branched amine is protected with Mtt is used for the peptide synthesis. During the procedure for the synthesis, Mtt is not removed under the basic conditions used for removal of Fmoc or Nsc. Thus synthesized peptide-resin (branched amine of targeted site is protected with Boc, branched amine of untargeted site, with Mtt, and N-terminal amine, with Fmoc or Nsc) is subjected to removal of Mtt on branched amine of untargeted site. Said deblocking can be carried out, for example, by treating with 1% TFA/MC(methylene chloride). At this time, the protecting group of amine at targeted site, Boc, is not removed. This peptide-resin (branched amine of targeted site is protected with Boc, N-terminal amine is protected with Fmoc or Nsc, and branched amine of untargeted site is exposed) is reacted with Fmoc-OSu or Nsc-OSu to protect branched amines of untargeted sites with Fmoc or Nsc, and then, the protecting group of amine at targeted site, Boc, is removed by cleavage solution (for example, TIS:water:TFA=2.5:2.5:95), to obtain selectively protected peptide(amine of targeted site is exposed and amines of untargeted sites are protected with Fmoc or Nsc).

Peptide in which amines of untargeted sites are protected with Boc can be prepared by method of protecting amine of targeted site with ivDde and amines of untargeted sites with Boc. In step of introducing lysine of targeted site, lysine in which $N^\alpha$-amine is protected with Fmoc or Nsc and branched amine is protected with ivDde is used, and in step of introducing lysine of other sites, lysine in which $N^\alpha$-amine is protected with Fmoc or Nsc and branched amine is protected with Boc is used for the peptide synthesis. During the synthesis, ivDde is not removed under deblocking condition of Fmoc or Nsc, for example, 1% DBU-20% piperidine/DMF. For the synthesized peptide-resin (branched amine of targeted site is protected with ivDde, branched amine of untargeted site, with Boc and N-terminal amine, with Fmoc or Nsc), removal of the N-terminal amine protecting group, Fmoc is performed (for example, by treatment with 1% DBU-20% piperidine in DMF) and then treated with cleavage solution (for example, TIS:water:TFA=2.5:2.5:95) to separate resin and peptide. At this time, a branched amine protecting group at targeted site, Boc is removed. Exposed amine of this peptide (branched amine of targeted site is protected with ivDde, and branched amine of untargeted site and N-terminal amine are exposed) is protected with Boc, and ivDde on amine of targeted site is removed, thereby obtaining peptide in which amines of untargeted sites are protected with Boc. At this time, said protection can be done, for example, by reacting with Boc₂O(di-tert-butyl dicarbonate), and said deblocking can be done, for example, by treatment with 2% hydrazine solution.

Peptides in which amines of untargeted sites are protected with Boc can be prepared by methods of protecting amine of targeted site with Mtt, and amines of untargeted sites with Boc. In this method, a resin extremely sensitive to acid such as 2-CLTR (2-chlorotrityl resin) should be used, and caution is required since yield and purity can be reduced due to moisture. In this method, in the step of introducing lysine of targeted site, lysine where $N^\alpha$-amine is protected with Fmoc or Nsc and branched amine is protected with Mtt is used, and in the step of introducing lysine of other sites, lysine where $N^\alpha$-amine is protected with Fmoc or Nsc and branched amine is protected with Boc is used for the peptide synthesis. During the synthesis, Mtt is not removed under the basic conditions used for removal of Fmoc or Nsc. Thus in synthesized peptide-resin (branched amine of targeted site is protected with Mtt, branched amine of untargeted site, with Boc, and N-terminal amine, with Fmoc or Nsc), removal of the protecting group of N-terminal amine, Fmoc or Nsc is conducted and protection of exposed $N^\alpha$-amine of N-terminus is performed with Boc. Said deblocking can be carried out, for example, by treating with 1% DBU-20% piperidine in DMF, and said protection can be conducted, for example, by reacting with Boc₂O. Thus synthesized peptide-resin (branched amine of targeted site is protected with Mtt, and amine(s) of untargeted sites are protected with Boc and C-terminus is combined to resin) is treated with TFA/MC to separate resin and peptide, and the protecting group of amine at targeted site, Mtt is removed, thereby obtaining peptide in which amine(s) of untargeted sites are protected with Boc. The protected peptide thus obtained is in a state where amines of untargeted sites are protected with Boc and active moiety except amine, i.e. hydroxyl or carboxyl group is protected and these protecting groups are to be removed at one time during the removal of Boc by cleavage solution (for instance, TIS:water:TFA=2.5:2.5:95) after PEGylation.

Besides said methods, various methods can be derived from the present invention, and these are also included in the present invention.

In addition, the peptide synthesized according to the present invention can be directly used for PEGylation, or can be employed for PEGylation, if necessary, after passing through additional step of protecting amines of untargeted site, including $N^\alpha$-amine with final amine protecting group. At this time, the final amine protecting group can be at least one selected from the group consisting of Fmoc, Nsc, Dde[1-(4,4-dimethyl-2,6-dioxocyclohexylidene)ethyl], ivDde or other protecting group removed under basic condition, or at least one protecting group selected from the group consisting of Boc or other protecting group removed under acidic condition.

The present invention further includes a method where peptide is separately synthesized by dividing the peptide into two or more fragments to raise efficiency of the peptide synthesis, and these are condensed to produce peptide in which amine(s) of untargeted sites are protected. Even in this case, protection-deblocking of the amine(s) is same as previously described, yet, as racemization may occur during condensation of fragments, thus this method can be effectively used for peptides which contain Gly or Pro that do not bring racemization upon condensation, in its amino acid sequence, and more useful in case of peptide whose synthesis or purification is difficult. In this method, for example, peptide synthesis is conducted by dividing the peptide into two fragments, i.e. one fragment of from N-terminus to Gly or Pro and the other fragment of from subsequent amino acid to C-terminus and the two fragments are condensed to form the peptide. A resin used for synthesis of fragment having N-terminal region should be extremely sensitive to acid so that TRT series resin is used, and upon completion of the synthesis of fragments, the fragments are separated from the resin under acidic condition while retaining other protecting group. A fragment having C-terminal region can be synthesized using conventional resin and condensed with N-terminal fragment while being combined to resin, and then can be separated from the resin, or C-terminal fragment can be synthesized using an acid-sensitive resin, separated from resin with protecting group being retained, and then subjected to condensation with N-terminal fragment in solution phase. In case the fragment is synthesized using an acid-sensitive resin and Mtt as a branched amine protecting group, and then separated from the resin, separation is conducted under the condition, AcOH:TFE(2,2,2-trifluoroethanol):MC(1:1:8) or TFE:MC(2:8) in order for Mtt not to be removed. In case branched amine of untargeted site in the N-terminal fragment is protected with ivDde, after condensation is completed, before separating peptide having full sequence from resin, protecting group can be substituted with Fmoc or Nsc. Additionally, in case amine at a targeted site is present on N-terminal fragment, separation from resin should be conducted under condition in which removal of Boc does not occur. C-terminal fragment is synthesized by the same method as in continuous synthesis.

As synthetic method for peptide that can be used in the present invention, there is no special limitation as long as it is compatible with the present invention, yet preferably, solid phase peptide synthesis is employed.

As the peptide to which the present invention can be applied, there is no special limitation as long as it is peptides having at least two branched amines. The present invention will be useful for peptides, which require extension of biological half-life or reduction of immunogenicity or antigenicity via combining PEGs to specific sites thereof. As an example, calcitonin or GRF(1-29) can be enumerated.

Peptides having protected amine(s) of untargeted sites enable completely specific PEGylation to peptide. Reacting peptide in which amine(s) of untargeted sites are protected with Fmoc, Nsc, Boc or other amine protecting groups stable under PEGylation condition, with activated PEGs leads to specific combining of PEGs to only amines at targeted sites and the reaction can almost complete in accordance with their equivalent ratio and reaction condition. Conducting deblocking {for example, 5% piperidine/DMF condition for protecting group, Fmoc or Nsc, and cleavage solution (TIS:water:TFA=2.5:2.5:95) for protecting group, Boc} of thus protected peptide-PEG conjugate (PEG are combined to amines of targeted sites and amines of untargeted sites are protected with protecting groups) leads to formation of peptide in which PEGs are specifically combined to amines at targeted sites.

Therefore, another embodiment of the present invention is methods for preparing specific PEG-conjugated peptide in which PEGs are specifically combined to amines of targeted sites, comprising (1) reacting the peptide in which amines at untargeted sites are selectively protected with activated PEGs and (2) amine protecting groups of thus obtained compound are removed under acid-base deblocking condition.

Said reaction mixture is confirmed not having other peptide-derived substance, and specifically conjugated PEG-peptide with high purity can be obtained by removing uncombined PEG and released protecting groups through ionic exchange chromatography, removing salts via reverse phase resin (e.g. C-18 Sep-Pak catridge), and subjecting to lyophilization.

Activated PEG that can conjugate with the peptide having selectively protected amines of untargeted sites, prepared according to the present invention, has no particular limitation and includes all the above mentioned PEG, yet, it is preferably linear or branched hydroxy- or methoxy-type alkylating or acylating PEG of 1,000 to 40,000, and more preferably, at least one selected from the group consisting of mono-methoxy poly(ethyleneglycol)succinimidyl succinate, mono-methoxy poly(ethyleneglycol)succinimidyl propionate, mono-methoxy poly(ethyleneglycol)succinimidyl carbonate, mono-methoxy poly(ethyleneglycol)succinimidyl carbamrate and mono-methoxy poly(ethyleneglycol)tresylate, can be used.

The specifically conjugated PEG-peptide of the present invention can be formulated into pharmaceutical dosage forms containing the peptide in therapeutically effective amount. Formulations such as injection, infusions, depot for injections, inhalations can be available, and buffering agents, tonicity regulating agents, stabilizers, surfactants, thickeners, preservatives, coloring agents and flavoring agents can be added.

BEST MODE FOR CARRYING OUT THE INVENTION

Figure 1:
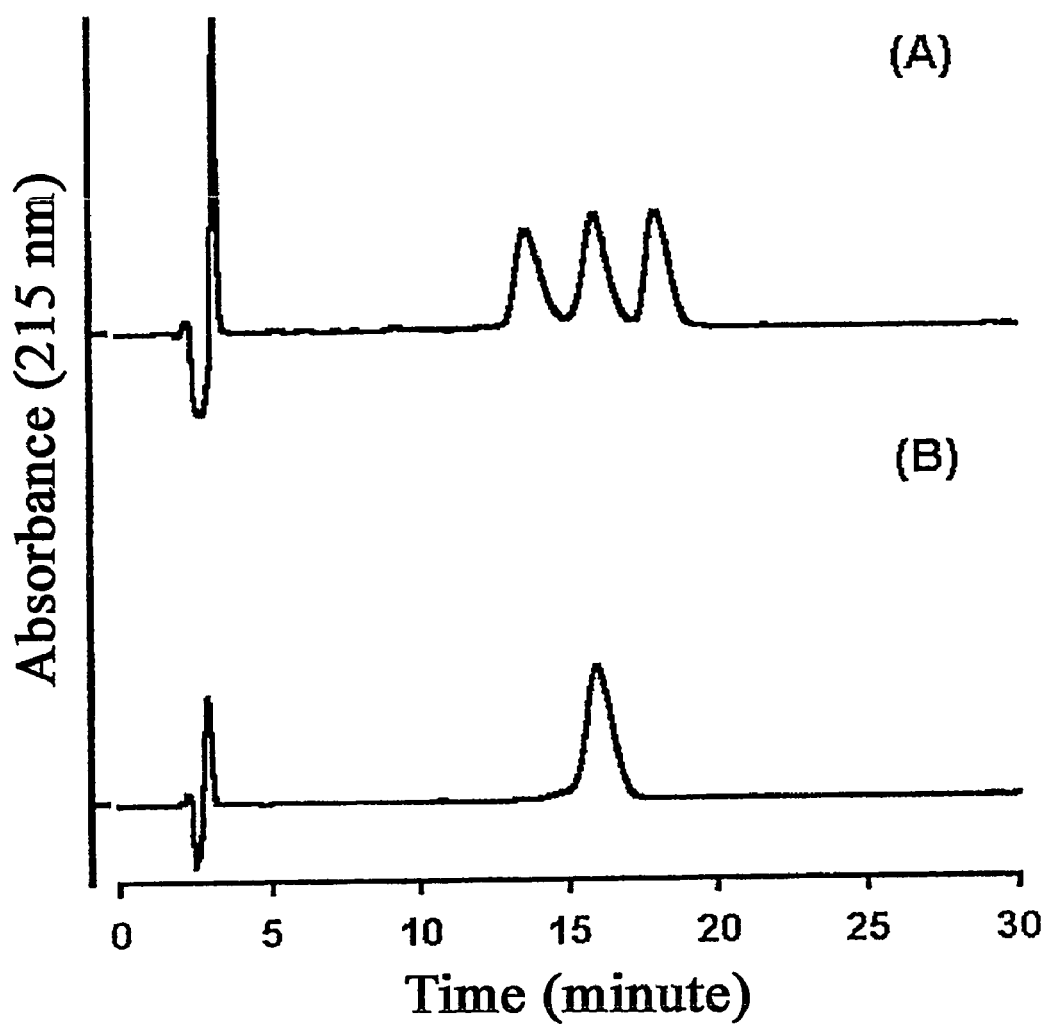
FIG. 1 represents reverse phase chromatograms for $Lys^{18}$-PEG 2K-salmon calcitonin in Example 20(B) and mono-PEG 2K-salmon calcitonin in Comparative Example 1(A).

In the below, detailed methods of the present invention are exemplified by Examples. However, the Examples are not intended to limit the scope of the present invention.

Abbreviations used in the present Examples define the following meaning. Ac=acetyl, $Ac_2O$= acetic anhydride, AcCN= acetonitrile, AcOH= acetic acid, Bop=benzotriazol-1-yloxy tris(dimethylamino)phosphonium hexafluorophosphate, Clt=2-chlorotrityl, DCM=dichloromethane, DIC= 1,3-diisopropylcarbodiimide, DIPEA=N,N-diisopropylethylamine, DMSO= dimethylsulfoxide, EDT=1,2-ethanedithiol, EtOAc= ethyl acetate, HBTU= N-[(1H-benzotriazol-1-yl)(dimethylamino)methylene]-N-methylmethaneammonium hexafluorophosphate N-oxide, HOBt=1-hydroxybenzotriazole, Pbf2,2,4,6,7-pentamethyldihydrobenzofuran-5-sulfonyl, Pmc=2,2,5,7,8-pentamethylchroman-6-sulfonyl, PyBop=benzotriazol-1-yloxytri(pyrrolidino)phosphonium hexafluorophosphate, SPPS= solid phase peptide synthesis, TBTU= N-[(1H-benzotriazol-1-yl)(dimethylamino)methylene]-N-methylmethaneammonium tetrafluoroborate N-oxide, tBu=tert-butyl, TEA=triethylamine, and Trt=tityl

EXAMPLE 1

Continuous synthesis of 1,11-diFmoc-salmon calcitonin using ivDde as a protecting group for branched amine of untargeted site Structure: Fmoc-$Cys^1$-Ser-Asn-Leu-Ser-Thr-$Cys^7$-Val-Leu-$Gly^{10}$-Lys(Fmoc)-Leu-Ser-Gln-Glu-Leu-His-Lys (Fmoc)-Leu-$Gln^{20}$-Thr-Tyr-Pro-Arg-Thr-Asn-Thr-Gly-Ser-$Gly^{30}$-Thr-Pro-$NH_2$ (1,7-disulfide bond)(SEQ ID NO:1)

TABLE 1

| Materials | MW | eq | mmols | grams | ml |
|---|---|---|---|---|---|
| Chain assembly (per coupling cycle*) | | | | | |
| Link-amide resin | — | 1.0 | 1.0 | 2.0 | — |
| Nsc-amino acid* | — | 1.5 | 1.5 | — | — |
| Fmoc-Lys(ivDde)-OH | 574.6 | 1.5 | 1.5 | 0.861 | — |
| DIPEA* | 129.3 | 3.0 | 3.0 | 0.387 | 0.52 |
| Bop* | 442.3 | 1.5 | 1.5 | 0.442 | — |
| HOBt* | 135.1 | 1.5 | 1.5 | 0.135 | — |
| DMF* | — | — | — | — | 4.0 |
| DCM* | — | — | — | — | 16.0 |
| 1% DBU-20% piperidine in DMF* | — | — | — | — | 40.0 |
| DMF(for each washing)* | — | — | — | — | 20.0 |
| Introduction of di-Fmoc | | | | | |
| 2% hydrazine hydrate in DMF | — | — | — | — | 60.0 |
| DMF | — | — | — | — | 240 |
| DCM | — | — | — | — | 160 |
| Fmoc-Osu | 337.3 | 5.0 | 10.0 | 3.37 | — |
| Oxidation | | | | | |
| 0.1M iodine in DMF | — | — | — | — | 50.0 |
| DMF (for oxidation) | — | — | — | — | 50.0 |
| 1.0M ascorbic acid in DMF | — | — | — | — | 250 |
| DMF | — | — | — | — | 310 |
| DCM | — | — | — | — | 60 |
| MeOH | — | — | — | — | 60 |
| Heptane | — | — | — | — | 60 |
| Cleavage | | | | | |
| TFA | — | — | — | — | 86 |
| TIS | — | — | — | — | 2.0 |
| Water | — | — | — | — | 2.0 |
| diethyl ether | — | — | — | — | 1100 |

*indicates the amount used per coupling cycle

Peptide was synthesized according to the following reaction order.

Reaction order: Nsc-Pro, Nsc-Thr(tBu), Nsc-Gly, Nsc-Ser (tBu), Nsc-Gly, Nsc-Thr(tBu), Nsc-Asn(Trt), Nsc-Thr(tBu), Nsc-Arg(Pbf), Nsc-Pro, Nsc-Tyr(tBu), Nsc-Thr(tBu), Nsc-Gln(Trt), Nsc-Leu, Nsc-Lys(Boc), Nsc-His(Trt), Nsc-Leu, Nsc-Glu(tBu), Nsc-Gln(Trt), Nsc-Ser(tBu), Nsc-Leu, Fmoc-Lys(ivDde), Nsc-Gly, Nsc-Leu, Nsc-Val, Nsc-Cys(Trt), Nsc-Thr(tBu), Nsc-Ser(tBu), Nsc-Leu, Nsc-Asn(Trt), Nsc-Ser (tBu), Nsc-Cys(trt)

2.0 g of link-amide resin was put in 50 ml peptide reaction vessel, 20 ml of DCM was poured and left for 30 min to allow the resin to sufficiently expand. The solution was removed via filtration. 20 ml of deblocking solution (1% DBU-20% piperidine in DMF) was added and reacted for 5 min (this process was repeated twice) to remove Fmoc, and washed 5 to 7 times with 20 ml DMF. Removal of remained piperidine and dibenzofulvene was confirmed with chloranil test [the test can be used to determine whether the removal of Nsc or Fmoc-related adducts and residual piperidine is complete. The test solution is prepared by adding a drop of a saturated solution of chloranil in toluene to about 1 ml of acetone. The DMF washing may be tested by adding a drop of the washing solution to the chloranil test solution. A blue or violet color is a positive indication for the presence of secondary amine].

To introduce C-terminal amino acid of calcitonin, Pro, Nsc-Pro-OH(1.5 eq), Bop(1.5 eq), HOBt(1.5 eq) and DIPEA (1.5 eq) were dissolved in 4 ml DMF and 8 ml DCM and put to said reactor containing the resin. The reaction solution was further washed with 8 ml DCM, added to the reactor, additional DIPEA(1.5 eq) was added, and reacted at 35° C. to 40° C. for 1 hr while mixing with an adequate blender. End point of the reaction was determined by Kaiser test [To check completion of the reaction using the qualitative ninhydrin test, a 2-10 mg sample of the resin is withdrawn and washed with ethanol. To the sample, 2 drops of 80% phenol solution, 2 drops of 0.02 mM KCN in pyridine and 2 drops of 5% ninhydrin in ethanol are added. The sample is left in a heat block at about 120° C. for 4 to 6 min. A blue or violet color is a positive indication of the presence of free amine], and in case the reaction did not reach completion, the reaction solution was further reacted for 30 min to 1 hr. Upon completion of the reaction, the reaction solution was removed by filtration, washed with 3×20 ml DMF, reacted with deblocking solution (2×20 ml) for 5 min in each time, and thoroughly washed with DMF.

Continuous introduction of amino acids was performed according to the method described above, and the reaction started from $Pro^{32}$ of C-terminus of calcitonin and proceeded in order, and after the introduction of protected amino acid, removal of Nsc or Fmoc was repeatedly conducted using deblocking solution. After Nsc-Cys(Trt) was introduced, the peptide was reacted with 3×20 ml of 2% hydrazine solution for 10-30 min to remove ivDde and Nsc, and then the resin was filtered and sufficiently washed with 4×20 ml DMF, 4×20 ml DCM and 4×20 ml DMF. Fmoc-OSu(5.0 eq) dissolved in 20 ml of DMF was put to the reactor, thoroughly mixed for 1 to 2 hr to allow Fmoc to be introduced to the amines on 1,11-positions, respectively. Progress of the reaction was checked by Kaiser test, and when determined as being completed, the reaction solution was removed via filtration, sufficiently washed with 4×20 ml DMF and 4×20 ml DCM, dried under-nitrogen stream to obtain peptide-attached resin 8.5 g.

1,7 disulfide bond could be formed by $I_2$ oxidation. The peptide resin obtained as above was put in 150 ml filterable peptide reactor, 50 ml DMF was poured and allowed to maintain equilibrium for 30 min. 0.1 M $I_2$ in 50 ml DMF was further added to the reactor, mixed well for 2 hrs to perform oxidation. Progress of the reaction was monitored with HPLC, and upon completion of the reaction, filtration and washing with 5×50 ml DMF and 5×50 ml ascorbic acid for 5 min in each time, was conducted to completely remove the residual $I_2$. Additionally, the peptide resin was washed with 3×20 ml DMF, 3×20 ml DCM, 3×20 ml MeOH and 3×20 ml heptane, dried under nitrogen, vacuum dried for 6 hrs to obtain dried peptide-attached resin 8.1 g.

Said dried resin was reacted with 80 ml cleavage solution (2.5:2.5:95=TIS:water:TFA) at ordinary temperature for 1.5 hr, the resin was removed and resulting peptide was washed with about 10 ml of TFA. The washing and filtrate were collected and added to 500 ml of ether, subjected to centrifuge to precipitate formed floating material, and additionally washed with 3×200 ml ether via centrifuge. The precipitate was dried under nitrogen to obtain dried peptide mixture 4.8 g, and this mixture was purified by prep-HPLC, and subjected to lyophilization to obtain 896 mg of 1,11-diFmoc-salmon calcitonin. Targeted site of the peptide prepared in this Example is the amine of $Lys^{18}$.

[Purification Conditions for Preparative HPLC]

Vydac protein & peptide-$C_{18}$, 20×250 mm, 5μ, 300 A

TFA buffered AcCN and water gradient

[Peptide Analysis Condition 1]

Instrument: Waters Alliance

Flow rate: 1.0 ml/min

Gradient: 0-45 min, B 0-100% (A: 0.1% TFA in water, B: 0.1% TFA in AcCN)

Column: Nova-Pak-$C_{18}$, 3.9 mm×150 mm, 5μ, 100 A

[Mass Analysis Condition]
Instrument: Voyager DE-STR Maldi Tof Mass(Perspective)
Mode of operation: Reflector
Extraction mode: Delayed
Polarity: Positive
Matrix: α-cyano-4-hydroxycinnamic acid
Maldi Tof; 3877.43, (M+1=3877.44) HPLC; 98% up (peptide analysis condition 1)

EXAMPLE 2

Continuous synthesis of 1,18-diFmoc-salmon calcitonin using ivDde as a protecting group for branched amine of untargeted site Structure: Fmoc-Cys$^1$-Ser-Asn-Leu-Ser-Thr-Cys$^7$-Val-Leu-Gly$^{10}$-Lys-Leu-Ser-Gln-Glu-Leu-His-Lys(Fmoc)-Leu-Gln$^{20}$-Thr-Tyr-Pro-Arg-Thr-Asn-Thr-Gly-Ser-Gly$^{30}$-Thr-Pro-NH$_2$ (1,7-disulfide bond)(SEQ ID NO.: 1)

TABLE 2

| Materials | MW | eq | mmols | grams | ml |
|---|---|---|---|---|---|
| Chain assembly (per coupling cycle*) | | | | | |
| Link-amide resin | — | 1.0 | 1.0 | 2.0 | — |
| Nsc-amino acid* | — | 1.5 | 1.5 | — | — |
| Fmoc-Lys(ivDde)-OH | 574.6 | 1.5 | 1.5 | 0.861 | — |
| DIPEA* | 129.3 | 3.0 | 3.0 | 0.387 | 0.52 |
| Bop* | 442.3 | 1.5 | 1.5 | 0.442 | — |
| HOBt* | 135.1 | 1.5 | 1.5 | 0.135 | — |
| DMF* | — | — | — | — | 4.0 |
| DCM* | — | — | — | — | 16.0 |
| 1% DBU-20% piperidine in DMF* | — | — | — | — | 40.0 |
| DMF(for each washing)* | — | — | — | — | 20.0 |
| Introduction of di-Fmoc | | | | | |
| 2% hydrazine hydrate in DMF | — | — | — | — | 60.0 |
| DMF | — | — | — | — | 240 |
| DCM | — | — | — | — | 160 |
| Fmoc-Osu | 337.3 | 5.0 | 10.0 | 3.37 | — |
| Oxidation | | | | | |
| 0.1M iodine in DMF | — | — | — | — | 50.0 |
| DMF (for oxidation) | — | — | — | — | 50.0 |
| 1.0M ascorbic acid in DMF | — | — | — | — | 250 |
| DMF | — | — | — | — | 310 |
| DCM | — | — | — | — | 60 |
| MeOH | — | — | — | — | 60 |
| heptane | — | — | — | — | 60 |
| Cleavage | | | | | |
| TFA | — | — | — | — | 86 |
| TIS | — | — | — | — | 2.0 |
| Water | — | — | — | — | 2.0 |
| diethyl ether | — | — | — | — | 1100 |

Reaction order: Nsc-Pro, Nsc-Thr(tBu), Nsc-Gly, Nsc-Ser(tBu), Nsc-Gly, Nsc-Thr(tBu), Nsc-Asn(Trt), Nsc-Thr(tBu), Nsc-Arg(Pbf), Nsc-Pro, Nsc-Tyr(tBu), Nsc-Thr(tBu), Nsc-Gln(Trt), Nsc-Leu, Fmoc-Lys(ivDde), Nsc-His(Trt), Nsc-Leu, Nsc-Glu(tBu), Nsc-Gln(Trt), Nsc-Ser(tBu), Nsc-Leu, Nsc-Lys(Boc), Nsc-Gly, Nsc-Leu, Nsc-Val, Nsc-Cys(Trt), Nsc-Thr(tBu), Nsc-Ser(tBu), Nsc-Leu, Nsc-Asn(Trt), Nsc-Ser(tBu), Nsc-Cys(trt).

Reaction was conducted according to the above Table and the reaction order of amino acid, as described in Example 1. When removal of ivDde and introduction of diFmoc and I$_2$ oxidation were performed, the peptide-attached resin was 8.2 g, and was treated with TFA-cleavage solution (2.5:2.5:95=TIS:water:TFA) as disclosed in Example 1 and purified by prep-HPLC to obtain 892 mg of 1,18-diFmoc-salmon calcitonin.

Maldi Tof; 3877.33, (M+1=3877.44) HPLC; 97% up (peptide analysis condition 1)

EXAMPLE 3

Continuous synthesis of 11,18-diFmoc-salmon calcitonin using ivDde as a protecting group for branched amine of untargeted site Structure: H-Cys$^1$-Ser-Asn-Leu-Ser-Thr-Cys$^7$-Val-Leu-Gly$^{10}$-Lys(Fmoc)-Leu-Ser-Gln-Glu-Leu-His-Lys-Leu-Gln$^{20}$-Thr-Tyr-Pro-Arg-Thr-Asn-Thr-Gly-Ser-Gly$^{30}$-Thr-Pro-NH$_2$ (1,7-disulfide bond)(SEQ ID NO:1)

TABLE 3

| Materials | MW | eq | mmols | grams | ml |
|---|---|---|---|---|---|
| Chain assembly (per coupling cycle*) | | | | | |
| Link-amide resin | — | 1.0 | 1.0 | 2.0 | — |
| Nsc-amino acid* | — | 1.5 | 1.5 | — | — |
| Fmoc-Lys(ivDde)-OH × 2 | 574.6 | 1.5 | 1.5 | 1.72 | — |
| Boc-Cys(trt)-OH | 463.6 | 1.5 | 1.5 | 0.695 | — |
| DIPEA* | 129.3 | 3.0 | 3.0 | 0.387 | 0.52 |
| Bop* | 442.3 | 1.5 | 1.5 | 0.442 | — |
| HOBt* | 135.1 | 1.5 | 1.5 | 0.135 | — |
| DMF* | — | — | — | — | 4.0 |
| DCM* | — | — | — | — | 16.0 |
| 1% DBU-20% piperidine in DMF* | — | — | — | — | 40.0 |
| DMF(for each washing*) | — | — | — | — | 20.0 |
| Introduction of di-Fmoc | | | | | |
| 2% hydrazine hydrate in DMF | — | — | — | — | 60.0 |
| DMF | — | — | — | — | 240 |
| DCM | — | — | — | — | 160 |
| Fmoc-OSu | 337.3 | 5.0 | 10.0 | 3.37 | — |
| Oxidation | | | | | |
| 0.1M iodine in DMF | — | — | — | — | 50.0 |
| DMF (for oxidation) | — | — | — | — | 50.0 |
| 1.0M ascorbic acid in DMF | — | — | — | — | 250 |
| DMF | — | — | — | — | 310 |
| DCM | — | — | — | — | 60 |
| MeOH | — | — | — | — | 60 |
| Heptane | — | — | — | — | 60 |
| Cleavage | | | | | |
| TFA | — | — | — | — | 86 |
| TIS | — | — | — | — | 2.0 |
| Water | — | — | — | — | 2.0 |
| diethyl ether | — | — | — | — | 1100 |

Reaction order: Nsc-Pro, Nsc-Thr(tBu), Nsc-Gly, Nsc-Ser(tBu), Nsc-Gly, Nsc-Thr(tBu), Nsc-Asn(Trt), Nsc-Thr(tBu), Nsc-Arg(Pbf), Nsc-Pro, Nsc-Tyr(tBu), Nsc-Thr(tBu), Nsc-Gln(Trt), Nsc-Leu, Fmoc-Lys(ivDde), Nsc-His(Trt), Nsc-Leu, Nsc-Glu(tBu), Nsc-Gln(Trt), Nsc-Ser(tBu), Nsc-Leu, Fmoc-Lys(ivDde), Nsc-Gly, Nsc-Leu, Nsc-Val, Nsc-Cys(Trt), Nsc-Thr(tBu), Nsc-Ser(tBu), Nsc-Leu, Nsc-Asn(Trt), Nsc-Ser(tBu), Boc-Cys(trt).

Reaction was conducted according to the above Table and the reaction order of amino acid, as described in Example 1. When removal of ivDde and introduction of diFmoc and I$_2$ oxidation were performed, the peptide-attached resin was 8.2 g, and was treated with TFA-cleavage solution (2.5:2.5:95=TIS:water:TFA) as disclosed in Example 1 and purified by prep-HPLC to obtain 890 mg of 11,18-diFmoc-salmon calcitonin.

Maldi Tof; 3877.23, (M+1=3877.44) HPLC; 98% up (peptide analysis condition 1)

EXAMPLE 4

Continuous synthesis of 1,12-diFmoc-GRF(1-29) using ivDde as a protecting group for branched amine of untargeted site Structure: Fmoc-Tyr-Ala-Asp-Ala-Ile-Phe-Thr-Asn-Ser-Tyr[10]-Arg-Lys(Fmoc)-Val-Leu-Gly-Gln-Leu-Ser-Ala-Arg[20]-Lys-Leu-Leu-Gln-Asp-Ile-Met-Ser-Arg-NH$_2$(SEQ ID NO.: 2)

TABLE 4

| Materials | MW | eq | mmols | grams | ml |
|---|---|---|---|---|---|
| Chain assembly (per coupling cycle*) | | | | | |
| Link-amide resin | — | 1.0 | 1.0 | 2.0 | — |
| Nsc-amino acid* | — | 1.5 | 1.5 | — | — |
| Fmoc-Lys(ivDde)-OH | 574.6 | 1.5 | 1.5 | 0.861 | — |
| DIPEA* | 129.3 | 3.0 | 3.0 | 0.387 | 0.52 |
| Bop* | 442.3 | 1.5 | 1.5 | 0.442 | — |
| HOBt* | 135.1 | 1.5 | 1.5 | 0.135 | — |
| DMF* | 73.10 | — | — | — | 4.0 |
| DCM* | 84.93 | — | — | — | 16.0 |
| 1% DBU-20% piperidine in DMF* | — | — | — | — | 40.0 |
| DMF(for each washing) | 73.10 | — | — | — | 20.0 |
| Introduction of di-Fmoc | | | | | |
| 2% hydrazine hydrate in DMF | — | — | — | — | 60.0 |
| DMF | 73.10 | — | — | — | 240 |
| DCM | 84.93 | — | — | — | 160 |
| Fmoc-Osu | 337.3 | 5.0 | 10.0 | 3.37 | — |
| Cleavage (resin 1 g) | | | | | |
| TFA | 114.02 | — | — | — | 11.5 |
| TIS | 158.36 | — | — | — | 0.25 |
| Water | 18.02 | — | — | — | 0.25 |
| EDT | 94.02 | — | — | — | 0.157 |
| TMS-Br | 153.10 | — | — | — | 0.130 |
| diethyl ether | 74.12 | — | — | — | 250 |

Reaction order: Nsc-Arg(pbf), Nsc-Ser(Trt), Nsc-Met, Nsc-Ile, Nsc-Asp(tBu), Nsc-Gln(Trt), Nsc-Leu, Nsc-Leu, Nsc-Lys(Boc), Nsc-Arg(Pbf), Nsc-Ala, Nsc-Ser(Trt), Nsc-Leu, Nsc-Gln(Trt), Nsc-Gly, Nsc-Leu, Nsc-Val, Fmoc-Lys(ivDde), Nsc-Arg(Pbf), Nsc-Tyr(tBu), Nsc-Ser(Trt), Nsc-Asn(Trt), Nsc-Thr(tBu), Nsc-Phe, Nsc-Ile, Nsc-Ala, Nsc-Asp(tBu), Nsc-Ala, Nsc-Tyr(tBu)

2.0 g of link-amide resin was put in 50 ml peptide reaction vessel, 20 ml DCM was poured and left for 30 min to allow resin to sufficiently expand. The solution was removed via filtration. 20 ml of deblocking solution (1% DBU-20% piperidine in DMF) was added and reacted for 5 min to remove Fmoc (this process was repeated twice), and washed 5-7 times with 20 ml DMF. Removal of remaining piperidine and dibenzofulvene was confirmed with chloranil test.

To introduce C-terminal amino acid of GRF(1-29), Arg, Nsc-Arg(Pbf)-OH(1.5eq), Bop(1.5eq), HOBt(1.5 eq) and DIPEA(1.5eq) were dissolved in 2ml DMF and 8 ml DCM and put in the reactor containing the resin. The reaction solution was washed with additional 8 ml DCM and pour to the reactor, DIPEA(1.5 eq) was further added, and the reaction was proceeded at 35° C. to 40° C. for 1 hr while mixing with an adequate blender. End point of the reaction was determined by Kaiser test, and in case the reaction did not complete, the reaction solution was further reacted for 30 min to 1 hr. Upon completion of the reaction, the reaction solution was removed by filtration, washed with 3×20 ml DMF, reacted with deblocking solution (2×20 ml) for 5 min in each time and thoroughly washed with DMF.

Continuous introduction of amino acids was performed as described above, and the reaction started from Arg of C-terminus of GRF(1-29) and proceeded in order, and after the introduction of protected amino acid, removal of NSc or Fmoc was repeatedly conducted using deblocking solution. After Nsc-Tyr(tBu) was introduced, reacted with 3×20 ml of 2% hydrazine solution for 10-30 min in each time to remove ivDde and Nsc, and then the resin was filtered and sufficiently washed with 4×20 ml DMF, 4×20, ml DCM and 4×20 ml DMF. Fmoc-OSu(5.0 eq) dissolved in 20 ml of DMF was put in the reactor, thoroughly mixed for 1 to 2 hr to allow Fmoc to be introduced to the amines on 1,12-positions, respectively. Progress of the reaction was checked by Kaiser test, and when determined completion of the reaction, the reaction solution was removed via filtration, sufficiently washed with 4×20 ml DMF and 4×20 ml DCM, dried under nitrogen stream to obtain peptide-attached resin 8.5 g.

1 g of said dried resin was withdrawn and reacted with 10 ml of cleavage solution (2.5:2.5:95=TIS:water:TFA) at ordinary temperature for 1.5 hr, and farther reacted with TMS-Br and EDT for 15 min. The resin was removed via filtration, and the resin was washed with 2 ml TFA. The washing and filtrate were collected and added to 100 ml of ether, subjected to centrifuge to precipitate formed floating material, and additionally washed with 3×50 ml ether via centrifuge. The precipitate was dried under nitrogen to obtain 690 mg of dried peptide mixture, and this mixture was purified by prep-HPLC, subjected to lyophilization to obtain 116 mg of 1,12-diFmoc-GRF(1-29).

Maldi Tof; 3803.39, (M+1=3803.46) HPLC; 96% up (peptide analysis condition 1)

EXAMPLE 5

Continuous synthesis of 1,21-diFmoc-GRF(1-29) using ivDde as a protecting group for branched amine of untargeted site Structure: Fmoc-Tyr-Ala-Asp-Ala-Ile-Phe-Thr-Asn-Ser-Tyr[10]-Arg-Lys-Val-Leu-Gly-Gln-Leu-Ser-Ala-Arg[20]-Lys(Fmoc)-Leu-Leu-Gln-Asp-Ile-Met-Ser-Arg-NH$_2$(SEQ ID NO.: 2)

TABLE 5

| Materials | MW | eq | mmols | grams | ml |
|---|---|---|---|---|---|
| Chain assembly (per coupling cycle*) | | | | | |
| Link-amide resin | — | 1.0 | 1.0 | 2.0 | — |
| Nsc-amino acid* | — | 1.5 | 1.5 | — | — |
| Fmoc-Lys(ivDde)-OH | 574.6 | 1.5 | 1.5 | 0.861 | — |
| DIPEA* | 129.3 | 3.0 | 3.0 | 0.387 | 0.52 |
| Bop* | 442.3 | 1.5 | 1.5 | 0.442 | — |
| HOBt* | 135.1 | 1.5 | 1.5 | 0.135 | — |
| DMF* | 73.10 | — | — | — | 4.0 |
| DCM* | 84.93 | — | — | — | 16.0 |
| 1% DBU-20% piperidine in DMF* | — | — | — | — | 40.0 |
| DMF(for each washing)* | 73.10 | — | — | — | 20.0 |
| Introduction of di-Fmoc | | | | | |
| 2% hydrazine hydrate in DMF | — | — | — | — | 60.0 |
| DMF | 73.10 | — | — | — | 240 |
| DCM | 84.93 | — | — | — | 160 |
| Fmoc-OSu | 337.3 | 5.0 | 10.0 | 3.37 | — |

TABLE 5-continued

| Materials | MW | eq | mmols | grams | ml |
|---|---|---|---|---|---|
| Cleavage (resin 1 g) | | | | | |
| TFA | 114.02 | — | — | — | 11.5 |
| TIS | 158.36 | — | — | — | 0.25 |
| Water | 18.02 | — | — | — | 0.25 |
| EDT | 94.02 | | | 0.157 | |
| TMS-Br | 153.10 | | | 0.130 | |
| diethyl ether | 74.12 | — | — | — | |

Reaction order: Nsc-Arg(pbf), Nsc-Ser(Trt), Nsc-Met, Nsc-Ile, Nsc-Asp(tBu), Nsc-Gln(Trt), Nsc-Leu, Nsc-Leu, Fmoc-Lys(ivDde), Nsc-Arg(Pbf), Nsc-Ala, Nsc-Ser(Trt), Nsc-Leu, Nsc-Gln(Trt), Nsc-Gly, Nsc-Leu, Nsc-Val, Nsc-Lys (Boc), Nsc-Arg(Pbf), Nsc-Tyr(tBu), Nsc-Ser(Trt), Nsc-Asn (Trt), Nsc-Thr(tBu), Nsc-Phe, Nsc-Ile, Nsc-Ala, Nsc-Asp (tBu), Nsc-Ala, Nsc-Tyr(tBu)

The reaction was conducted as described in Example 4 by using the reagents and solvent given in the above Table. Introduction of DiFmoc could be achieved by use of Fmoc-Osu (3.37 g in 20 ml DMF) after the removal of ivDde with 2% hydrazine in DMF according to the method as in Example 4, and after the reaction, 7.9 g as dried resin was obtained. 1 g of thus obtained peptide resin was withdrawn, mixed and reacted with 10 ml of cleavage solution (2.5:2.5:95=TIS/water/TFA) for 1.5 hr, and additional EDT(0.130 ml) and TMS-Br(0.157 ml) were added to the reaction solution and further stirred for 15 min. The reaction solution was treated with ether as in Example 4 to obtain 710 mg of peptide mixture, and through prep-HPLC purification, 86 mg of 1,21-diFmoc GRF(1-29) was obtained.

Maldi Tof; 3803.59, (M+1=3803.46) HPLC; 98% up (peptide analysis condition 1)

EXAMPLE 6

Continuous synthesis of 12,21-diFmoc-GRF(1-29) using ivDde as a protecting group for branched amine of untargeted site Structure: H-Tyr-Ala-Asp-Ala-Ile-Phe-Thr-Asn-Ser-Tyr[10]-Arg-Lys(Fmoc)-Val-Leu-Gly-Gln-Leu-Ser-Ala-Arg[20]-Lys(Fmoc)-Leu-Leu-Gln-Asp-Ile-Met-Ser-Arg-NH$_2$ (SEQ ID NO.: 2)

TABLE 6

| Materials | MW | eq | mmols | grams | ml |
|---|---|---|---|---|---|
| Chain assembly (per coupling cycle*) | | | | | |
| Link-amide resin | — | 1.0 | 1.0 | 2.0 | — |
| Nsc-amino acid* | — | 1.5 | 1.5 | — | — |
| Fmoc-Lys(ivDde)-OH | 574.6 | 1.5 | 1.5 | 0.861 | — |
| DIPEA* | 129.3 | 3.0 | 3.0 | 0.387 | 0.52 |
| Bop* | 442.3 | 1.5 | 1.5 | 0.442 | — |
| HOBt* | 135.1 | 1.5 | 1.5 | 0.135 | — |
| DMF* | 73.10 | — | — | — | 4.0 |
| DCM* | 84.93 | — | — | — | 16.0 |
| 1% DBU-20% piperidine in DMF* | — | — | — | — | 40.0 |
| DMF(for each washing)* | 73.10 | — | — | — | 20.0 |
| Introduction of di-Fmoc | | | | | |
| 2% hydrazine hydrate in DMF | — | — | — | — | 60.0 |
| DMF | 73.10 | — | — | — | 240 |
| DCM | 84.93 | — | — | — | 160 |
| Fmoc-OSu | 337.3 | 5.0 | 10.0 | 3.37 | — |

TABLE 6-continued

| Materials | MW | eq | mmols | grams | ml |
|---|---|---|---|---|---|
| Cleavage(resin 1 g) | | | | | |
| TFA | 114.02 | — | — | — | 11.5 |
| TIS | 158.36 | — | — | — | 0.25 |
| Water | 18.02 | — | — | — | 0.25 |
| EDT | 94.02 | | | 0.157 | |
| TMS-Br | 153.10 | | | 0.130 | |
| diethyl ether | 74.12 | — | — | — | 250 |

Reaction order: Nsc-Arg(pbf), Nsc-Ser(Trt), Nsc-Met, Nsc-Ile, Nsc-Asp(tBu), Nsc-Gln(Trt), Nsc-Leu, Nsc-Leu, Nsc-Lys(ivDde), Nsc-Arg(Pbf), Nsc-Ala, Nsc-Ser(Trt), Nsc-Leu, Nsc-Gln(Trt), Nsc-Gly, Nsc-Leu, Nsc-Val, Fmoc-Lys (ivDde), Nsc-Arg(Pbf), Nsc-Tyr(tBu), Nsc-Ser(Trt), Nsc-Asn(Trt), Nsc-Thr(tBu), Nsc-Phe, Nsc-Ile, Nsc-Ala, Nsc-Asp(tBu), Nsc-Ala, Boc-Tyr(tBu)

The reaction was conducted as described in Example 4 by using the reagents and solvent given in the above Table. Introduction of DiFmoc could be achieved by use of Fmoc-OSu(3.37 g in 20 ml DMF) after the removal of ivDde with 2% hydrazine in DMF according to the method as in Example 4, and after the reaction, 8.4 g as dried resin was obtained. 1 g of thus obtained peptide resin was withdrawn, mixed and reacted with 10 ml of cleavage solution (2.5:2.5:95=TIS/water/TFA) for 1.5 hr, and additional EDT(0.130 ml) and TMS-Br(0.157 ml) were added to the reaction solution and further stirred for 15 min. The reaction solution was treated with ether as in Example 4 to obtain 710 mg of peptide mixture, and through prep-HPLC purification, 86 mg of 12,21-diFmoc GRF(1-29) was obtained.

Maldi Tof; 3803.39, (M+1=3803.46) HPLC; 96% up (peptide analysis condition 1)

EXAMPLE 7

Continuous synthesis of 1,12-diNsc-GRF(1-29) using ivDde as a protecting group for branched amine of untargeted site Structure: Nsc-Tyr-Ala-Asp-Ala-Ile-Phe-Thr-Asn-Ser-Tyr[10]-Arg-Lys(Nsc)-Val-Leu-Gly-Gln-Leu-Ser-Ala-Arg[20]-Lys-Leu-Leu-Gln-Asp-Ee-Met-Ser-Arg-NH$_2$ (SEQ ID NO.: 2)

TABLE 7

| Materials | MW | eq | mmols | grams | Ml |
|---|---|---|---|---|---|
| Chain assembly (per coupling cycle*) | | | | | |
| Link-amide resin | — | 1.0 | 1.0 | 2.0 | — |
| Nsc-amino acid* | — | 1.5 | 1.5 | — | — |
| Fmoc-Lys(ivDde)-OH | 574.6 | 1.5 | 1.5 | 0.861 | — |
| DIPEA* | 129.3 | 3.0 | 3.0 | 0.387 | 0.52 |
| Bop* | 442.3 | 1.5 | 1.5 | 0.442 | — |
| HOBt* | 135.1 | 1.5 | 1.5 | 0.135 | — |
| DMF* | 73.10 | — | — | — | 4.0 |
| DCM* | 84.93 | — | — | — | 16.0 |
| 1% DBU-20% piperidine in DMF* | — | — | — | — | 40.0 |
| DMF(for each washing)* | 73.10 | — | — | — | 20.0 |
| Introduction of di-Nsc | | | | | |
| 2% hydrazine hydrate in DMF | — | — | — | — | 60.0 |
| DMF | 73.10 | — | — | — | 240 |
| DCM | 84.93 | — | — | — | 160 |
| Nsc-Osu | 372.3 | 5.0 | 10.0 | 3.72 | — |

TABLE 7-continued

| Materials | MW | eq | mmols | grams | Ml |
|---|---|---|---|---|---|
| Cleavage (resin 1 g) | | | | | |
| TFA | 114.02 | — | — | — | 11.5 |
| TIS | 158.36 | — | — | — | 0.25 |
| water | 18.02 | — | — | — | 0.25 |
| EDT | 94.02 | | | | 0.157 |
| TMS-Br | 153.10 | | | | 0.130 |
| diethyl ether | 74.12 | — | — | — | 250 |

Reaction order: Nsc-Arg(pbf), Nsc-Ser(Trt), Nsc-Met, Nsc-Ile, Nsc-Asp(tBu), Nsc-Gln(Trt), Nsc-Leu, Nsc-Leu, Nsc-Lys(Boc) Nsc-Arg(Pbf), Nsc-Ala, Nsc-Ser(Trt), Nsc-Leu, Nsc-Gln(Trt), Nsc-Gly, Nsc-Leu, Nsc-Val, Fmoc-Lys (ivDde), Nsc-Arg(Pbf), Nsc-Tyr(tBu), Nsc-Ser(Trt), Nsc-Asn(Trt), Nsc-Thr(tBu), Nsc-Phe, Nsc-Ile, Nsc-Ala, Nsc-Asp(tBu), Nsc-Ala, Nsc-Tyr(tBu)

The synthesis was conducted as described in Example 4 by using the reagents and solvent given in the above Table. Introduction of DiNsc could be achieved by use of Nsc-OSu (3.72 g in 20 ml DMF), after the removal of ivDde with 2% hydrazine in DMF according to the method as in Example 4, and after the reaction, 8.1 g as dried resin was obtained. 1 g of thus obtained peptide resin was withdrawn, mixed and reacted with 10 ml of cleavage solution (2.5:2.5:95=TIS:water:TFA) for 1.5 hr, and additional EDT(0.130 ml) and TMS-Br(0.157 ml) were added to the reaction solution and further stirred for 15 min. The reaction solution was treated with ether as in Example 4 to obtain 700 mg of peptide mixture, and through prep-HPLC purification, 136 mg of 1,12-diNsc GRF(1-29) was obtained.

Maldi Tof; 3874.46, (M+1=3874.39) HPLC; 98% up (peptide analysis condition 1)

EXAMPLE 8

Continuous synthesis of 1,12-di(ivDde)-GRF(1-29) using ivDde as a protecting group for branched amine of untargeted site Structure: ivDde-Tyr-Ala-Asp-Ala-Ile-Phe-Thr-Asn-Ser-Tyr$^{10}$-Arg-Lys(ivDde)-Val-Leu-Gly-Gln-Leu-Ser-Ala-Arg$^{20}$-Lys-Leu-Leu-Gln-Asp-Ile-Met-Ser-Arg-NH$_2$ (SEQ ID NO : 2)

TABLE 8

| Materials | MW | eq | mmols | grams | Ml |
|---|---|---|---|---|---|
| Chain assembly (per coupling cycle*) | | | | | |
| Link-amide resin | — | 1.0 | 1.0 | 2.0 | — |
| Nsc-amino acid* | — | 1.5 | 1.5 | — | — |
| Fmoc-Lys(ivDde)-OH | 574.6 | 1.5 | 1.5 | 0.861 | — |
| DIPEA* | 129.3 | 3.0 | 3.0 | 0.387 | 0.52 |
| Bop* | 442.3 | 1.5 | 1.5 | 0.442 | — |
| HOBt* | 135.1 | 1.5 | 1.5 | 0.135 | — |
| DMF* | 73.10 | — | — | — | 4.0 |
| DCM* | 84.93 | — | — | — | 16.0 |
| 1% DBU-20% piperidine in DMF* | — | — | — | — | 40.0 |
| DMF(for each washing) | 73.10 | — | — | — | 20.0 |
| Introduction of ivDde | | | | | |
| DMF | 73.10 | — | — | — | 20 |
| ivDde-OH (2-isovaleryldimedone) | 226.3 | — | — | 1.0 | — |

TABLE 8-continued

| Materials | MW | eq | mmols | grams | Ml |
|---|---|---|---|---|---|
| Cleavage (resin 1 g) | | | | | |
| TFA | 114.02 | — | — | — | 11.5 |
| TIS | 158.36 | — | — | — | 0.25 |
| water | 18.02 | — | — | — | 0.25 |
| EDT | 94.02 | | | | 0.157 |
| TMS-Br | 153.10 | | | | 0.130 |
| diethyl ether | 74.12 | — | — | — | 250 |

Reaction order: Nsc-Arg(pbf), Nsc-Ser(Trt), Nsc-Met, Nsc-Ile, Nsc-Asp(tBu), Nsc-Gln(Trt), Nsc-Leu, Nsc-Leu, Nsc-Lys(Boc), Nsc-Arg(Pbf), Nsc-Ala, Nsc-Ser(Trt), Nsc-Leu, Nsc-Gln(Trt), Nsc-Gly, Nsc-Leu, Nsc-Val, Fmoc-Lys (ivDde), Nsc-Arg(Pbf), Nsc-Tyr(tBu), Nsc-Ser(Trt), Nsc-Asn(Trt), Nsc-Thr(tBu), Nsc-Phe, Nsc-Ile, Nsc-Ala, Nsc-Asp(tBu), Nsc-Ala, Nsc-Tyr(tBu)

The synthesis was conducted as described in Example 4 by using the reagents and solvent given in the above Table. After reaction with Nsc-Tyr(tBu) and subsequent removal of the Nsc, introduction of ivDde to the N-terminus could be achieved by reaction with 2-isovaleryldimedone(1.0 g in 20 ml DMF) for 12 hrs, and as a result of the reaction, 8.1 g as dried resin was obtained. 1 g of the peptide resin was withdrawn, mixed and reacted with 10 ml of cleavage solution (2.5:2.5:95=TIS:water:TFA) for 1.5 hr, and additional EDT (0.130 ml) and TMS-Br(0.157 ml) were added to the reaction solution and further stirred for 15 min. The reaction solution was treated with ether as in Example 4 to obtain 680 mg of peptide mixture, and through prep-HPLC purification, 97 mg of 1,12-di(ivDde)-GRF(1-29) was obtained.

Maldi Tof; 3771.39, (M+1=3771.55) HPLC; 94% up (peptide analysis condition 1)

EXAMPLE 9

Continuous synthesis of 1,12-diBoc-GRF(1-29) using ivDde as a protecting group for branched amine of untargeted site

Example 9-1

Synthesis of 21-Nsc-GRF(1-29)

Structure: H-Tyr-Ala-Asp-Ala-Ile-Phe-Thr-Asn-Ser-Tyr$^{10}$-Arg-Lys-Val-Leu-Gly-Gln-Leu-Ser-Ala-Arg$^{20}$-Lys(Nsc)-Leu-Leu-Gln-Asp-Ile-Met-Ser-Arg-NH$_2$ (SEQ ID NO.: 2)

TABLE 9

| Materials | MW | eq | mmols | grams | Ml |
|---|---|---|---|---|---|
| Chain assembly (per coupling cycle*) | | | | | |
| Link-amide resin | — | 1.0 | 1.0 | 2.0 | — |
| Nsc-amino acid* | — | 1.5 | 1.5 | — | — |
| Fmoc-Lys(ivDde)-OH | 574.6 | 1.5 | 1.5 | 0.861 | — |
| DIPEA* | 129.3 | 3.0 | 3.0 | 0.387 | 0.52 |
| Bop* | 442.3 | 1.5 | 1.5 | 0.442 | — |
| HOBt* | 135.1 | 1.5 | 1.5 | 0.135 | — |
| DMF* | 73.10 | — | — | — | 4.0 |
| DCM* | 84.93 | — | — | — | 16.0 |
| 1% DBU-20% piperidine in DMF* | — | — | — | — | 40.0 |
| DMF(for each washing)* | 73.10 | — | — | — | 20.0 |

TABLE 9-continued

| Materials | MW | eq | mmols | grams | Ml |
|---|---|---|---|---|---|
| Introduction of Nsc | | | | | |
| 2% hydrazine hydrate in DMF | — | — | — | — | 60.0 |
| DMF | 73.10 | — | — | — | 240 |
| DCM | 84.93 | — | — | — | 160 |
| Nsc-Osu | 372.3 | 5.0 | 5.0 | 3.72 | — |
| Cleavage (resin 1 g) | | | | | |
| TFA | 114.02 | — | — | — | 80 |
| TIS | 158.36 | — | — | — | 2.0 |
| Water | 18.02 | — | — | — | 2.0 |
| EDT | 94.02 | | | | 1.26 |
| TMS-Br | 153.10 | | | | 1.04 |
| diethyl ether | 74.12 | — | — | — | 2000 |

Reaction order: Nsc-Arg(pbf), Nsc-Ser(Trt), Nsc-Met, Nsc-Ile, Nsc-Asp(tBu), Nsc-Gln(Trt), Nsc-Leu, Nsc-Leu, Fmoc-Lys(ivDde), Nsc-Arg(Pbf), Nsc-Ala, Nsc-Ser(Trt), Nsc-Leu, Nsc-Gln(Trt), Nsc-Gly, Nsc-Leu, Nsc-Val, Nsc-Lys (Boc), Nsc-Arg(Pbf), Nsc-Tyr(tBu), Nsc-Ser(Trt), Nsc-Asn (Trt), Nsc-Thr(tBu), Nsc-Phe, Nsc-Ile, Nsc-Ala, Nsc-Asp (tBu), Nsc-Ala, Boc-Tyr(tBu)

The synthesis was conducted as described in Example 4 by using the reagents and solvent given in the above Table. Introduction of Nsc could be achieved according to method as in Example 4 by use of Nsc-OSu(3.72 g in 20 ml DMF), after removal of ivDde with 2% hydrazine in DMF, and after the reaction, 7.5 g as dried resin was obtained. Thus obtained peptide resin was reacted with 80 ml of cleavage solution (2.5:2.5:95=TIS:water:TFA) for 1.5 hr, and additional EDT (1.26 ml) and TMS-Br(1.04 ml) were added to the reaction solution and further stirred for 15 min. The reaction solution was treated with ether as in Example 4 to obtain 4.1 g of peptide mixture, and through prep-HPLC purification, 520 mg of 21-Nsc-GRF(1-29) was obtained.

Maldi Tof; 3616.39, (M+1=3616.17) HPLC; 98% up (peptide analysis condition 1)

Example 9-2

Synthesis of 1,12-diBoc-GRF(1-29)

Structure: Boc-Tyr-Ala-Asp-Ala-Ile-Phe-Thr-Asn-Ser-Tyr$^{10}$-Arg-Lys(Boc)-Val-Leu-Gly-Gln-Leu-Ser-Ala-Arg$^{20}$-Lys-Leu-Leu-Gln-Asp-Ile-Met-Ser-Arg-NH$_2$ (SEQ ID NO.: 2)

TABLE 10

| Materials | MW | eq | mmols | grams | Ml |
|---|---|---|---|---|---|
| 21-Fmoc-GRF(1-29) | — | 1.0 | 0.1 | 0.36 | — |
| Boc2O | 218.3 | | | 1.0 | |
| DMF | | — | — | — | 10 |
| 5% Na$_2$CO$_3$ | | — | — | — | 10 |
| hexane | | — | — | — | 150 |
| methyl tert-butyl ether(MTBE) | | — | — | — | 60 |

360 mg of the synthesized 21-Nsc-GRF(1-29) and 5 ml of DMF were put in 25 ml-single neck reactor with magnetic stirrer and dissolved. The reactant was allowed to place under air-blocked environment by use of nitrogen gas, temperature was lowered to 0 to 5° C. with ice bath. To the reaction solution, Boc$_2$O (1 g/5 ml DMF) was added dropwise 0 to 5° C., the temperature was maintained for about 10 min, the ice bath was removed to allow the temperature to slowly reach to ordinary temperature. While keeping stirring for 3 to 4 hrs, progress of reaction was monitored with HPLC (peptide analysis condition 1) by collecting sample every hour. Upon completion of reaction, 5% Na$_2$CO$_3$ 10 ml was added dropwise to the reaction solution with stirring not to cause precipitation. The reaction was proceeded for about 30 min and progress of the removal of Nsc was checked with HPLC. The reaction solution was concentrated to ¼ fold, washed with 150 ml of hexane to obtain tacky oil. To this oil, 20 ml of MTBE was poured and left for 12 hrs to lead to precipitation, and this precipitation was separated from centrifuge. It was further washed with 2×20 ml MTBE and dried under nitrogen to obtain 330 mg of 1,12-diBoc-GRF(1-29).

Maldi Tof; 3559.21, (M+1=3559.20) HPLC; 92% up (peptide analysis condition 1)

EXAMPLE 10

Continuous synthesis of 1,12-di(Dde)-GRF(1-29) using Dde as a protecting group for branched amine of untargeted site Structure: Dde-Tyr-Ala-Asp-Ala-Ile-Phe-Thr-Asn-Ser-Tyr$^{10}$-Arg-Lys(Dde)-Val-Leu-Gly-Gln-Leu-Ser-Ala-Arg$^{20}$-Lys-Leu-Leu-Gln-Asp-Ile-Met-Ser-Arg-NH$_2$ (SEQ ID NO.: 2)

TABLE 11

| Materials | MW | eq | mmols | grams | ml |
|---|---|---|---|---|---|
| Chain assembly (per coupling cycle*) | | | | | |
| Link-amide resin | — | 1.0 | 1.0 | 2.0 | — |
| Nsc-amino acid* | — | 1.5 | 1.5 | | — |
| Fmoc-Lys(Dde)-OH | 532.6 | 1.5 | 1.5 | 0.799 | — |
| DIPEA* | 129.3 | 3.0 | 3.0 | 0.387 | 0.52 |
| Bop* | 442.3 | 1.5 | 1.5 | 0.442 | — |
| HOBt* | 135.1 | 1.5 | 1.5 | 0.135 | — |
| DMF* | 73.10 | — | — | — | 4.0 |
| DCM* | 84.93 | — | — | — | 16.0 |
| 1% DBU-20% piperidine in DMF* | — | — | — | — | 40.0 |
| DMF(for each washing)* | 73.10 | — | — | — | 20.0 |
| Introduction of Dde | | | | | |
| DMF | 73.10 | — | — | — | 20 |
| Dde-OH (2-acetyldimedone) | 184.2 | — | — | 1.0 | — |
| Cleavage (resin 1 g) | | | | | |
| TFA | 114.02 | — | — | — | 11.5 |
| TIS | 158.36 | — | — | — | 0.25 |
| water | 18.02 | — | — | — | 0.25 |
| EDT | 94.02 | | | | 0.157 |
| TMS-Br | 153.10 | | | | 0.130 |
| diethyl ether | 74.12 | — | — | — | 250 |

Reaction order: Nsc-Arg(pbf), Nsc-Ser(Trt), Nsc-Met, Nsc-Ile, Nsc-Asp(tBu), Nsc-Gln(Trt), Nsc-Leu, Nsc-Leu, Nsc-Lys(Boc), Nsc-Arg(Pbf), Nsc-Ala, Nsc-Ser(Trt), Nsc-Leu, Nsc-Gln(Trt), Nsc-Gly, Nsc-Leu, Nsc-Val, Fmoc-Lys (Dde), Nsc-Arg(Pbf), Nsc-Tyr(tBu), Nsc-Ser(Trt), Nsc-Asn (Trt), Nsc-Thr(tBu), Nsc-Phe, Nsc-Ile, Nsc-Ala, Nsc-Asp (tBu), Nsc-Ala, Nsc-Tyr(tBu)

The synthesis was conducted as described in Example 4 by using the reagents and solvent given in the above Table. After reaction with Nsc-Tyr(tBu) and removal of the Nsc, introduction of Dde to the N-terminus could be achieved by reaction with 2-acetyldimedone(1.0 g in 20 ml DMF) for 6 hrs, and after the reaction, 8.8 g as dried resin was obtained. 1 g of the peptide resin was withdrawn and reacted with 10 ml of cleavage solution (2.5:2.5:95=TIS/water/TFA) for 1.5 hr, and additional EDT(0.130 ml) and TMS-Br(0.157 ml) were added to the reaction solution and further stirred for 15 min. The reaction solution was treated with ether as in Example 4 to obtain 590 mg of peptide mixture, and through prep-HPLC purification, 104 mg of 1,12-diDde-GRF(1-29) was obtained.

Maldi Tof; 3687.69, (M+1=3687.55) HPLC; 95% up (peptide analysis condition 1)

EXAMPLE 11

Continuous synthesis of 1,11-diFmoc-salmon calcitonin using Mtt as a protecting group for branched amine of untargeted site Structure: Fmoc-Cys$^1$-Ser-Asn-Leu-Ser-Thr-Cys$^7$-Val-Leu-Gly$^{10}$-Lys(Fmoc)-Leu-Ser-Gln-Glu-Leu-His-Lys-Leu-Gln$^{20}$-Thr-Tyr-Pro-Arg-Thr-Asn-Thr-Gly-Ser-Gly$^{30}$-Thr-Pro-NH$_2$ (SEQ ID NO.: 1)(1,7-disulfide bond)

TABLE 12

| Materials | MW | Eq | mmols | grams | ml |
|---|---|---|---|---|---|
| Chain assembly (per coupling cycle*) | | | | | |
| Link-amide resin | — | 1.0 | 1.0 | 2.0 | — |
| Nsc-amino acid* | — | 1.5 | 1.5 | — | — |
| Fmoc-Lys(Mtt)-OH | 624.8 | 1.5 | 1.5 | 0.937 | — |
| Fmoc-Cys(Trt)-OH | 585.7 | 1.5 | 1.5 | 0.879 | — |
| DIPEA* | 129.3 | 3.0 | 3.0 | 0.387 | 0.52 |
| Bop* | 442.3 | 1.5 | 1.5 | 0.442 | — |
| HOBt* | 135.1 | 1.5 | 1.5 | 0.135 | — |
| DMF* | — | — | — | — | 4.0 |
| DCM* | — | — | — | — | 16.0 |
| 1% DBU-20% piperidine in DMF,* | — | — | — | — | 40.0 |
| DMF(for each washing)* | — | — | — | — | 20.0 |
| Introduction of di-Fmoc | | | | | |
| 1% TFA in DCM | — | — | — | — | 60.0 |
| DMF | — | — | — | — | 260 |
| DCM | — | — | — | — | 160 |
| Fmoc-Osu | 337.3 | 5.0 | 10.0 | 3.37 | — |
| Oxidation | | | | | |
| 0.1M iodine in DMF, | — | — | — | — | 50.0 |
| DMF (for oxidation) | — | — | — | — | 50.0 |
| 1.0M ascorbic acid in DMF | — | — | — | — | 250 |
| DMF | — | — | — | — | 310 |
| DCM | — | — | — | — | 60 |
| MeOH | — | — | — | — | 60 |
| heptane | — | — | — | — | 60 |
| Cleavage | | | | | |
| TFA | — | — | — | — | 86 |
| TIS | — | — | — | — | 2.0 |
| water | — | — | — | — | 2.0 |
| diethyl ether | — | — | — | — | 1100 |

Reaction order: Nsc-Pro, Nsc-Thr(tBu), Nsc-Gly, Nsc-Ser(tBu), Nsc-Gly, Nsc-Thr(tBu), Nsc-Asn(Trt), Nsc-Thr(tBu), Nsc-Arg(Pbf), Nsc-Pro, Nsc-Tyr(tBu), Nsc-Thr(tBu), Nsc-Gln(Trt), Nsc-Leu, Nsc-Lys(Boc), Nsc-His(Trt), Nsc-Leu, Nsc-Glu(tBu), Nsc-Gln(Trt), Nsc-Ser(tBu), Nsc-Leu, Fmoc-Lys(Mtt), Nsc-Gly, Nsc-Leu, Nsc-Val, Nsc-Cys(Trt), Nsc-Thr(tBu), Nsc-Ser(tBu), Nsc-Leu, Nsc-Asn(Trt), Nsc-Ser(tBu), Fmoc-Cys(trt)

2.0 g of link-amide resin was put in 50 ml peptide reactor, 20 ml DCM was poured and left for 30 min to allow resin to sufficiently expand. The solution was removed via filtration. Fmoc was removed by reaction with 2×20 ml deblocking solution (1% DBU-20% piperidine in DMF) for 5 min in each time, and washed 5-7 times with 20 ml DMF. Removal of remaining piperidine and dibenzofulvene was checked with chloranil test.

To introduce C-terminal amino acid of calcitonin, Pro, Nsc-Pro-OH(1.5 eq), Bop(1.5 eq), HOBt(1.5 eq) and DIPEA (1.5 eq) were dissolved in 4 ml DMF and 8 ml DCM and put in the reactor containing the resin. The reaction solution was further washed with 8 ml DCM, added to the reactor, and additional DIPEA(1.5 eq) was added, reacted at 35° C. to 40° C. for about 1 hr under thoroughly mixing with an adequate blender. End point of the reaction was determined by Kaiser test, and in case the reaction did not complete, the reaction solution was further reacted for 30 min to 1 hr. Upon completion of the reaction, the reaction solution was removed by filtration, washed with 3×20 ml DMF, reacted with deblocking solution (2×20 ml) for 5 min in each time, and thoroughly washed with DMF.

Continuous introduction of amino acids was performed according to the method described above, and the reaction started from Pro$^{32}$ of C-terminus of calcitonin and proceeded in order, and coupling reaction and deblocking was repeated according to the order. Repeated reaction as explained above, coupling reaction and deblocking can be conducted by using automatic instrument. Lastly, after Fmoc-Cys(Trt) was introduced to the N-terminus, the resin was washed with DCM. The resin was reacted with 3×20 ml 1% TFA solution for 10 to 30 min in each time to remove Mtt at 11-position. The removal of Mtt was confirmed by TLC analysis based on reactivity of the reaction solution to UV and TFA fume in comparison with blank. Upon completion of reaction, the resin was filtered and sufficiently washed with 4×20 ml DMF, 4×20 ml DCM and 4×20 ml DMF. Fmoc-OSu(5.0 eq) dissolved in 20 ml DMF was put into the reactor, thoroughly mixed for 1 to 2 hr to allow Fmoc to be introduced to Lys at 11-position. Progress of the reaction was checked by Kaiser test, when determined as being completed, the reaction solution was removed via filtration, sufficiently washed with 4×20 ml DMF and 4×20 ml DCM, and dried under nitrogen stream to obtain peptide-attached resin 8.5 g.

1,7 disulfide bond could be formed by I$_2$ oxidation. The peptide resin obtained as above was put in 150 ml filterable peptide reactor, 50 ml DMF was poured and allowed to maintain equilibrium for 30 min. Additional 0.1M I$_2$ in 50 ml DMF was added to the reactor, mixed well for 2 hrs to perform oxidation. Progress of the reaction was monitored with HPLC, and upon completion of the reaction, filtration and washing with 5×50 ml DMF and 5×50 ml ascorbic acid for 5 min in each time, were conducted to completely remove residual I$_2$. Additionally, the resulting product was washed with 3×20 ml DMF, 3×20 ml DCM, 3×20 ml MeOH and 3×20 ml heptane, dried under nitrogen, vacuum-dried for 6 hrs to obtain dried peptide-attached resin 8.1 g.

The dried resin was reacted with 80 ml cleavage solution (2.5:2.5:95=TIS:water:TFA) at ordinary temperature for 1.5 hr, the resin was removed and washed with about 10 ml of TFA. The washing and filtrate were collected and added to 500 ml of ether, subjected to centrifuge to precipitate the formed precipitate, and additionally centrifuged and washed with 3×200 ml ether. The precipitate was dried under nitrogen to obtain dried peptide mixture 4.8 g, and this mixture was purified by prep-HPLC, subjected to lyophilization to obtain 896 mg of 1,11-diFmoc-salmon calcitonin.

Maldi Tof; 3877.43, (M+1=3877.44) HPLC; 98% up (peptide analysis condition 1)

EXAMPLE 12

Continuous synthesis of 1,12-diFmoc-GRF(1-29) using Mtt as a protecting group for branched amine of untargeted site Structure: Fmoc-Tyr-Ala-Asp-Ala-Ile-Phe-Thr-Asn-Ser-Tyr$^{10}$-Arg-Lys(Fmoc)-Val-Leu-Gly-Gln-Leu-Ser-Ala-Arg$^{20}$-Lys-Leu-Leu-Gln-Asp-Ile-Met-Ser-Arg-NH$_2$(SEQ ID NO.: 2)

TABLE 13

| Materials | MW | eq | mmols | grams | ml |
|---|---|---|---|---|---|
| Chain assembly (per coupling cycle*) | | | | | |
| Link-amide resin | — | 1.0 | 1.0 | 2.0 | — |
| Nsc-amino acid* | — | 1.5 | 1.5 | — | — |
| Fmoc-Lys(Mtt)-OH | 624.8 | 1.5 | 1.5 | 0.937 | — |
| Fmoc-Tyr(tBu)-OH | 459.6 | 1.5 | 1.5 | 0.689 | — |
| DIPEA* | 129.3 | 3.0 | 3.0 | 0.387 | 0.52 |
| Bop* | 442.3 | 1.5 | 1.5 | 0.442 | — |
| HOBt* | 135.1 | 1.5 | 1.5 | 0.135 | — |
| DMF* | 73.10 | — | — | — | 4.0 |
| DCM* | 84.93 | — | — | — | 16.0 |
| 1% DBU-20% piperidine in DMF* | — | — | — | — | 40.0 |
| DMF(for each washing)* | 73.10 | — | — | — | 20.0 |
| Introduction of di-Fmoc | | | | | |
| 1% TFA in DCN | — | — | — | — | 60.0 |
| DMF | 73.10 | — | — | — | 260 |
| DCM | 84.93 | — | — | — | 160 |
| Fmoc-Osu | 337.3 | 5.0 | 10.0 | 3.37 | — |
| Cleavage (resin 1 g) | | | | | |
| TFA | 114.02 | — | — | — | 11.5 |
| TIS | 158.36 | — | — | — | 0.25 |
| Water | 18.02 | — | — | — | 0.25 |
| EDT | 94.02 | — | — | — | 0.157 |
| TMS-Br | 153.10 | — | — | — | 0.130 |
| diethyl ether | 74.12 | — | — | — | 250 |

Reaction order: Nsc-Arg(pbf), Nsc-Ser(Trt), Nsc-Met, Nsc-Ile, Nsc-Asp(tBu), Nsc-Gln(Trt), Nsc-Leu, Nsc-Leu, Nsc-Lys(Boc), Nsc-Arg(Pbf), Nsc-Ala, Nsc-Ser(Trt), Nsc-Leu, Nsc-Gln(Trt), Nsc-Gly, Nsc-Leu, Nsc-Val, Fmoc-Lys (Mtt), Nsc-Arg(Pbf), Nsc-Tyr(tBu), Nsc-Ser(Trt), Nsc-Asn (Trt), Nsc-Thr(tBu), Nsc-Phe, Nsc-Ile, Nsc-Ala, Nsc-Asp (tBu), Nsc-Ala, Fmoc-Tyr(tBu)

2 g of link-amide resin was put in 50 ml peptide reactor, 20 ml DCM was poured and left 30 min to allow the resin to sufficiently expand. The solution was removed via filtration. Fmoc was removed by reaction with 2×20 ml deblocking solution (1% DBU-20% piperidine in DMF) for 5 min in each time, and washed 5-7 times with 20 ml DMF. Removal of remaining piperidine and dibenzofulvene was confirmed with chloranil test.

To introduce C-terminal amino acid of GRF(1-29), Arg, Nsc-Arg(Pbf)-OH(1.5 eq), Bop(1.5 eq), HOBt(1.5 eq) and DIPEA(1.5 eq) were dissolved in 4 ml DMF and 8 ml DCM and put in the reactor containing the resin. The reaction solution was further washed with 8 ml DCM, added to the reactor, and additional DIPEA(1.5 eq) was added, reacted at 35° C. to 40° C. for about 1 hr under thoroughly mixing with an adequate blender. End point of the reaction was determined by Kaiser test, and in case the reaction did not complete, the reaction solution was further reacted for 30 min to 1 hr. Upon completion of the reaction, the reaction solution was removed by filtration, washed with 3×20 ml DMF, reacted with deblocking solution (2×20 ml) for 5 min in each time, and thoroughly washed with DMF.

Continuous introduction of amino acids was performed according to the method described above, and the reaction started from Arg of the C-terminus of GRF(1-29) and proceeded in order, and coupling reaction and deblocking were repeated in accordance with the order. Repeated reaction as explained above, coupling reaction and deblocking can be conducted by using automatic instrument. After Fmoc-Tyr (tBu) was introduced to the N-terminus, the resin was washed with DCM and soaked in 20 ml DCM for about 15 min. After DCM was removed, the resin was reacted with 3×20 ml 1% TFA solution for 10 to 30 min in each time, to remove Mtt at 12-position. The removal of Mtt was confirmed by TLC analysis based on reactivity of the reaction solution to UV and TFA fume in comparison with blank. Upon completion of reaction, the resin was filtered and sufficiently washed with 4×20 ml DMF, 4×20 ml DCM and 4×20 ml DMF. Fmoc-OSu (5.0 eq) dissolved in 20 ml DMF was put into the reactor, thoroughly mixed for 1 to 2 hr to allow Fmoc to be introduced to Lys at 12-position. Progress of the reaction was checked by Kaiser test, when determined as being completed, the reaction solution was removed via filtration, sufficiently washed with 4×20 ml DMF and 4×20 ml DCM, dried under nitrogen stream to obtain peptide-attached resin 8.5 g.

1 g of the dried resin was withdrawn and reacted with 10 ml cleavage solution (2.5:2.5:95=TIS: water: TFA) at ordinary temperature for 1.5 hr, and additionally reacted with TMS-Br and EDT for 15 min. The resin was removed via filtration, washed with about 2 ml TFA. The washing and filtrate were collected and added to 100 ml of ether, subjected to centrifuge to precipitate the formed floating material, and additionally centrifuged and washed with 3×50 ml ether. The precipitate was dried under nitrogen to obtain dried peptide mixture 690 mg, and this mixture was purified by prep-HPLC, subjected to lyophilization to obtain 116 mg of 1,12-diFmoc-GRF(1-29).

Maldi Tof; 3803.39, (M+1=3803.46) HPLC; 96% up (peptide analysis condition 1)

EXAMPLE 13

Frgament condensation synthesis of 1,11-diFmoc-salmon calcitonin using ivDde as a protecting group for branched amine of untargeted site Example 13-1

Synthesis of Nsc-Gly-2-ClTrt-resin

TABLE 14

| Materials | MW | eq | mmols | grams | ml |
|---|---|---|---|---|---|
| Chain assembly (per coupling cycle)* | | | | | |
| 2-chlorotrityl resin | — | — | — | 10.0 | — |
| Nsc-Gly | 332.30 | 1.0 | 10.0 | 3.32 | — |
| DIPEA | 129.30 | 3.0 | 30.0 | 3.88 | 9.22 |
| DCM | | | | | 768 |
| MeOH | | | | | 8 |

10 g of 2-CLTR resin was put into 250 ml peptide reactor, 100 ml DCM was poured and allowed the resin to sufficiently expand for 30 min, and then the solution was removed via filtration. Nsc-Gly-OH(3.32 g) and DIPEA(5.22 ml) were dissolved in 100 ml DCM, the solution was put to the reactor containing the resin, mixed at ordinary temperature for about 1 hr to allow the reaction to be proceeded. The reaction solution was removed via filtration, washed with 100 ml DCM, reacted with 80 ml DCM:MeOH:DIPEA(17:2:1) for 20 min to remove active moiety of the resin by substituting with MeOH. After washing with 4×100 ml DCM, subjected to drying under nitrogen to obtain Nsc-Gly-CLTR 13.1 g {UV-spectrum assay (instrument: BioRad Smart Spec 3000, Extinction coefficient of Nsc: 2000 $cm^{-}M^{-1}$ at 300 nm; capacity 0.61 mmol/g)}.

Example 13-2

Synthesis of Nsc-AA$^{sCt}$(1-10)-OH

Structure: Nsc-Cys$^1$-Ser(tBu)-Asn(Trt)-Leu-Ser(tBu)-Thr(tBu)-Cys$^7$-Val-Leu-Gly$^{10}$-OH (1,7-disulfide bond) (SEQ ID NO.: 3)

TABLE 15

| Materials | MW | eq | mmols | grams | ml |
|---|---|---|---|---|---|
| Chain assembly (per coupling cycle*) | | | | | |
| Nsc-Gly-2-CLTR | — | 1.0 | 5.0 | 8.2 | — |
| Nsc-amino acid* | — | 1.5 | 7.5 | — | — |
| DIPEA* | 129.3 | 3.0 | 15.0 | 1.94 | 2.61 |
| Bop* | 442.3 | 1.5 | 7.5 | 3.32 | — |
| HOBt* | 135.1 | 1.5 | 7.5 | 1.01 | — |
| DMF* | — | — | — | — | 4.0 |
| DCM* | — | — | — | — | 16.0 |
| 1% DBU-20% piperidine in DMF* | — | — | — | — | 100 |
| DMF(for each washing)* | — | — | — | — | 50.0 |
| Oxidation | | | | | |
| 0.1M iodine in DCM | — | — | — | — | 250.0 |
| DCM(for oxidation) | — | — | — | — | 250.0 |
| DMF | — | — | — | — | 800 |
| MeOH | — | — | — | — | 300 |
| DCM | — | — | — | — | 300 |
| heptane | — | — | — | — | 300 |
| Cleavage | | | | | |
| TFA | — | — | — | — | 2.0 |
| pyridine | — | — | — | — | 2.0 |
| DCM | — | — | — | — | 250 |
| ethanol | — | — | — | — | 50 |
| water | — | — | — | — | 200 |

8.2 g of Nsc-Gly-2-CLTR (capacity 0.61 mmol/g) synthesized as above was put in 200 ml peptide reactor, 50 ml of DCM was poured and left for 30 min to allow the reaction mixture to reach equilibrium. DCM was removed via filtration, and 2×50 ml deblocking solution (1% DBU-20% piperidine in DMF) was reacted for 5 min in each time, and washed thoroughly with 5×50 ml of DMF. According to the sequence of peptide, coupling and deblocking was repeatedly conducted as described in Example 1 starting from C-terminus by using reagents shown in the above Table. The reaction order was Leu, Val, Cys(Trt), Thr(tBu), Ser(tBu), Leu, Asn(Trt), Ser(tBu) and Cys(Trt), and after condensation of Nsc-Cys(Trt)-OH, the Nsc was not removed for subsequent reaction.

1,7 disulfide bond could be formed by I2 oxidation. The peptide resin obtained as above was put in 800 ml filterable peptide reactor, 250 ml DCM was poured and allowed to maintain equilibrium for 30 min. Additional 0.1M $I_2$ in 250 ml DCM was added to the reactor, mixed well for 2 hrs to perform oxidation. Progress of the reaction was monitored with HPLC (peptide analysis condition 2), and upon completion of the reaction, filtration and washing with 5×100 ml DMF for 10 min in each time, was conducted to completely remove residual $I_2$. Additionally, the reaction product was washed with 3×100 ml DMF, 3×100 ml DCM, 3×100 ml MeOH and 3×100 ml heptane, dried under nitrogen, and vacuum-dried for 6 hrs to obtain 16.9 g of dried peptide-attached resin.

The peptide was released under mild acidic condition with protecting group being maintained, the peptide was treated with 1% TFA in 150 ml DCM for 2 min and filtered, and thus obtained solution was treated with 0.5% TFA in 100 ml DCM for 1 min, and this solution was immediately neutralized by pyridine in an amount equal to the consumed TFA. This solution was vacuum concentrated to ¼ volume, treated with 50 ml ethanol, and subjected to re-concentration to final volume of about 50 ml. Water (100 ml) was added to this solution to precipitate, and the precipitate was separated via centrifuge, and the precipitate was washed with 2×50 ml water. The precipitate was sufficiently dried under vacuum to obtain 6.8 g of Nsc-AA$^{sCt}$(1-10)-OH (93% HPLC purity).

[Peptide Analysis Condition 2]
Instrument: Waters Alliance
Flow rate: 1.0 ml/min
Gradient: 0-50 min, B 40-100% (A: 0.1% TFA in water, B: 0.1% TFA in AcCN)
Column: Nova-Pak-$C_{18}$, 3.9 mm×150 mm, 5μ, 100 A
Maldi Tof; 1663.23, (M+1=1662.09) HPLC; 93% up (peptide analysis condition 2)

Example 13-3

Synthesis of 11-N$^\alpha$-Fmoc-11-ivDde-18-Boc-AA$^{sCt}$ (11-32)-link amide resin Structure: Fmoc-Lys(ivDde)-Leu-Ser(tBu)-Gln(Trt)-Glu(tBu)-Leu-His(Trt)-Lys(Boc)-Leu-Gln(Trt)-Thr(tBu)-Tyr(tBu)-Pro-Arg(Pbf)Thr(tBu)-Asn(Trt)-Thr(tBu)-Gly-Ser(tBu)-Gly-Thr(tBu)-Pro-link amide resin(SEQ ID NO.: 4)

TABLE 16

| Materials | MW | eq | mmols | grams | ml |
|---|---|---|---|---|---|
| Chain assembly (per coupling cycle*) | | | | | |
| Link-amide resin | — | 1.0 | 1.0 | 2.0 | — |
| Nsc-amino acid* | — | 1.5 | 1.5 | — | — |
| Fmoc-Lys(ivDde)-OH | 574.6 | 1.5 | 1.5 | 0.861 | — |
| DIPEA* | 129.3 | 3.0 | 3.0 | 0.387 | 0.52 |
| Bop* | 442.3 | 1.5 | 1.5 | 0.442 | — |
| HOBt* | 135.1 | 1.5 | 1.5 | 0.135 | — |
| DMF* | — | — | — | — | 4.0 |
| DCM* | — | — | — | — | 16.0 |
| 1% DBU-20% piperidine in DMF* | — | — | — | — | 40.0 |
| DMF(for each washing)* | — | — | — | — | 20.0 |

2.0 g of link amide resin was put in peptide reactor, 20 ml of DCM was poured and left for 30 min to allow the reaction to reach equilibrium. Removal of Fmoc attached to the resin was conducted by reacting with 2×20 ml of deblocking solution (1% DBU-20% piperidine in DMF) for 5 min in each time, and washed the resin thoroughly with 5×20 ml of DMF. According to the sequence of peptide, condensation and deblocking was repeatedly conducted as described in Example 1 starting from C-terminus by using reagents shown in the above Table. The reaction order was Pro, Thr(tBu), Gly, Ser(tBu), Gly, Thr(tBu), Asn(Trt), Thr(tBu), Arg(Pbf), Pro, Tyr(tBu), Thr(tBu), Gln (Trt), Leu, Lys(Boc), His(Trt), Leu, Glu(tBu), Gln (Trt), Ser(tBu), Leu and Lys(ivDde). After carrying out condensation of Fmoc-Lys(ivDde)-OH, while allowing the Fmoc to be maintained, the resin was washed with 4×20 ml DMF and 4×20 ml DCM, dried under nitrogen to obtain 6.5 g of peptide-attached resin (UV spectrum assay; capacity 0.14 mmol/g).

Example 13-4

Synthesis of 1,11-diFmoc-salmon calcitonin based on condensation of Nsc-AA$^{sCt}$(1-10)-OH and Fmoc-AA$^{sCt}$(11-32)-link amide resin Structure: Fmoc-Cys$^1$-Ser-Asn-Leu-Ser-Thr-Cys$^7$-Val-Leu-Gly$^{10}$-Lys(Fmoc)-Leu-Ser-Gln-Glu-Leu-His-Lys-Leu-Gln$^{20}$-Thr-Tyr-Pro-Arg-Thr-Asn-Thr-Gly-Ser-Gly$^{30}$-Thr-Pro-NH$_2$(SEQ ID NO.: 1)(1,7-disulfide bond)

TABLE 17

| Materials | MW | eq | mmols | grams | ml |
|---|---|---|---|---|---|
| Deblocking | | | | | |
| Fmoc-AA$^{sCt}$(11-32)-link amide resin (above) | — | 1.0 | 0.5 | 3.57 | — |
| DCM | | | | | 30 |
| 1% DBU-20% piperidine in DMF | — | — | — | — | 40.0 |
| DMF(for each washing) | — | — | — | — | 180 |
| Fragment condensation | | | | | |
| H-AA$^{sCt}$(11-32)-link amide resin (above) | — | 1.0 | 0.5 | — | — |
| Nsc-AAsCt (1-10)-OH (2.2) | 1662 | 1.5 | 0.75 | 1.25 | — |
| DIPEA | 129.3 | 3.0 | 1.5 | 0.194 | 0.26 |
| Bop | 442.3 | 1.5 | 0.75 | 0.332 | — |
| HOBt | 135.1 | 1.5 | 0.80 | 0.108 | — |
| DMF | — | — | — | — | 4.0 |
| DCM | — | — | — | — | 16.0 |
| 1% DBU-20% piperidine in DMF | — | — | — | — | 20.0 |
| DMF(for each washing) | — | — | — | — | 20.0 |
| Introduction of diFmoc | | | | | |
| 2% hydrazine hydrate in DMF | — | — | — | — | 60.0 |
| DMF | — | — | — | — | 240 |
| DCM | — | — | — | — | 160 |
| Fmoc-OSu | 337.3 | 5.0 | 10.0 | 3.37 | — |
| Cleavage | | | | | |
| TFA | — | — | — | — | 38 |
| TIS | — | — | — | — | 1.0 |
| water | — | — | — | — | 1.0 |
| diethyl ether | — | — | — | — | 500 |

Fmoc-AA$^{sCt}$(11-32)-link amide resin (3.85 g) prepared as described above was put into peptide reactor, allowed to sufficiently expand with 30 ml DCM. Solution within the reactor was removed, and treated with 2×20 ml deblocking solution (1% DBU-20% piperidine in DMF) for 5 min in each time to remove Fmoc, and sufficiently washed 7-9 times with 20 ml of DMF while checking removal of residual by chloranil test.

The peptide fragment Nsc-AA$^{sCt}$(1-10)-OH (1.25 g) prepared in the above was dissolved in 4 ml DMF, HOBt(0.108 g) and DIPEA(0.160 ml) were put and the temperature of the reaction solution was lowered to 0-5° C. using an ice bath. Under nitrogen, Bop(0.332 g) was put to the reaction solution and mixed well for 10 min while the temperature was maintained at 0-5° C. The reaction solution was poured to the peptide reactor in which the resin was placed and mixed by shaking for 10 min, and DIPEA(0.100 ml) was added. Reaction was proceeded at ordinary temperature for about 12 hr and progress of reaction was determined based on Kaiser test and analytical HPLC(peptide analysis condition 1). Upon completion of reaction, the resin was washed with 3×20 ml DMF, treated with 2% hydrazine 3×20 ml for 10-30 m/v in to remove base-labile Nsc and ivDde. The removal of ivDde was confirmed from TLC analysis for which the treated solution and 2% hydrazine solution were spotted, respectively, on TLC plate and their UV absorbance was compared. Upon completion of removal, the resin was filtered and washed with 4×20 ml DMF, 4×20 ml DCM, 3×20 ml DMF, and Fmoc-Osu (3.37 g in 20 ml DMF) was added and reacted for 2 hrs to introduce diFmoc. The introduction of Fmoc was checked by qualitative Kaiser test, and the resin was washed with 4×20 ml DMF and 4×20 ml DCM, dried under nitrogen to obtain 4.3 g of peptide attached resin.

Reaction solution obtained by reacting the resin obtained as above with 40 ml of TFA-cleavage solution (2.5:2.5:95=TIS:water:TFA) at ordinary temperature for about 2 hrs, was filtered, added to 300 ml of cold ether to induce precipitation of peptide. The precipitate was separated via centrifuge, further washed with 2×100 ml of ether and dried to obtain 2.6 g of peptide mixture. The peptide mixture was purified by prep-HPLC, concentrated and dried with a freeze dryer to obtain 1036 mg of 1,11-diFmoc-salmon calcitonin.

Maldi Tof; 3877.41, (M+1=3877.44) HPLC; 98% up (peptide analysis condition 1)

EXAMPLE 14

Fragment condensation synthesis of 1,11-diNsc-salmon calcitonin using ivDde as a protecting group for branched amine of untargeted site Structure: Nsc-Cys$^1$-Ser-Asn-Leu-Ser-Thr-Cys$^7$-Val-Leu-Gly$^{10}$-Lys(Nsc)-Leu-Ser-Gln-Glu-Leu-His-Lys-Leu-Gln$^{20}$-Thr-Tyr-Pro-Arg-Thr-Asn-Thr-Gly-Ser-Gly$^{30}$-Thr-Pro-NH$_2$ (1,7-disulfide bond)(SEQ ID NO.: 1)

TABLE 18

| Materials | MW | eq | mmols | grams | ml |
|---|---|---|---|---|---|
| Deblocking | | | | | |
| Fmoc-AAsCt(11-32)-Link-amide resin (Example 13) | — | 1.0 | 0.5 | 3.57 | — |
| DCM | | | | | 30 |
| 1% DBU-20% piperidine in DMF | — | — | — | — | 40.0 |
| DMF(for each washing) | — | — | — | — | 200 |
| Fragment condensation | | | | | |
| H-AAsCt (11-32)-link-amide resin (above) | — | 1.0 | 0.5 | — | — |
| Nsc-AAsCt (1-10)-OH (Example 13) | 1662 | 1.5 | 0.75 | 1.25 | — |
| DIPEA | 129.3 | 3.0 | 1.5 | 0.194 | 0.26 |
| Bop | 442.3 | 1.5 | 0.75 | 0.332 | — |
| HOBt | 135.1 | 1.5 | 0.80 | 0.108 | — |
| DMF | — | — | — | — | 4.0 |
| DCM | — | — | — | — | 16.0 |
| 1% DBU-20% piperidine in DMF | — | — | — | — | 20.0 |
| DMF(for each washing) | — | — | — | — | 20.0 |
| Introduction of diNsc | | | | | |
| 2% hydrazine hydrate in DMF | — | — | — | — | 60.0 |
| DMF | — | — | — | — | 240 |

TABLE 18-continued

| Materials | MW | eq | mmols | grams | ml |
|---|---|---|---|---|---|
| DCM | — | — | — | — | 160 |
| Nsc-OSu | 372.3 | 5.0 | 10.0 | 3.72 | — |
| Cleavage | | | | | |
| TFA | — | — | — | — | 38 |
| TIS | — | — | — | — | 1.0 |
| water | — | — | — | — | 1.0 |
| diethyl ether | — | — | — | — | 500 |

Fragment condensation was conducted according to the method as in Example 13 by using Fmoc-AA$^{sCt}$(11-32)-link amide resin (3.57 g) and Nsc-AA$^{sCt}$(1-10)-OH prepared in Example 13 and the solvents and reagents shown in the above Table, and diNsc was introduced by reaction with Nsc-OSu (3.72 g in 20 ml DMF) to obtain peptide attached resin 4.8 g. Peptide mixture obtained from said peptide attached resin and TFA cleavage solution (2.5:2.5:95=TIS:water:TFA) was separated and purified to obtain 1228 mg of 1,11-diNsc salmon calcitonin.

Maldi Tof; 3947.40, (M+1=3947.38) HPLC; 98% up (peptide analysis condition 1)

EXAMPLE 15

Fragment condensation synthesis of 1,18-diFmoc-salmon calcitonin using ivDde as a protecting group for branched amine of untargeted site

Example 15-1

Synthesis of 11-N$^\alpha$-Nsc-11-Boc-18-ivDde-AA$^{sCt}$ (11-32)-link amide resin Structure: Nsc-Lys(Boc)-Leu-Ser(tBu)-Gln(Trt)-Glu(tBu)-Leu-His(Trt)-Lys(ivDde)-Leu-Gln(Trt)-Thr(tBu)-Tyr(tBu)-Pro-Arg(Pbf)-Thr(tBu)-Asn(Trt)-Thr(tBu)-Gly-Ser(tBu)-Gly-Thr(tBu)-Pro-link amide resin (SEQ ID NO.: 4)

TABLE 19

| Materials | MW | eq | mmols | grams | ml |
|---|---|---|---|---|---|
| Chain assembly (per coupling cycle*) | | | | | |
| Link-amide resin | — | 1.0 | 1.0 | 2.0 | — |
| Nsc-amino acid* | — | 1.5 | 1.5 | — | — |
| Fmoc-Lys(ivDde)-OH | 574.6 | 1.5 | 1.5 | 0.861 | — |
| DIPEA* | 129.3 | 3.0 | 3.0 | 0.387 | 0.52 |
| Bop* | 442.3 | 1.5 | 1.5 | 0.442 | — |
| HOBt* | 135.1 | 1.5 | 1.5 | 0.135 | — |
| DMF* | — | — | — | — | 4.0 |
| DCM* | — | — | — | — | 16.0 |
| 1% DBU-20% piperidine in DMF* | — | — | — | — | 20.0 |
| DMF(for each washing)* | — | — | — | — | 20.0 |

Reaction order: Nsc-Pro, Nsc-Thr(tBu), Nsc-Gly, Nsc-Ser(tBu), Nsc-Gly, Nsc-Thr(tBu), Nsc-Asn(Trt), Nsc-Thr(tBu), Nsc-Arg(Pbf), Nsc-Pro, Nsc-Tyr(tBu), Nsc-Thr(tBu), Nsc-Gln(Trt), Nsc-Leu, Fmoc-Lys(ivDde), Nsc-His(Trt), Nsc-Leu, Nsc-Glu(tBu), Nsc-Gln(Trt), Nsc-Ser(tBu), Nsc-Leu, Nsc-Lys(Boc)

Synthesis was conducted according to the same method as in synthesis of Fmoc-AA$^{sCt}$(11-32)-link amide resin of Example 13, and as a result, 6.8 g of well-dried resin was obtained and peptide capacity of the resin was determined as 0.13 mmol/g by UV spectrum analysis (UV-spectrum assay; capacity 0.13 mmol/g).

Example 15-2

Synthesis of 1,18-diFmoc-salmon calcitonin based on condensation of Nsc-AA$^{sCt}$(1-10)-OH with Nsc-AA$^{sCt}$(11-32)-link amide resin Structure: Fmoc-Cys$^1$-Ser-Asn-Leu-Ser-Thr-Cys$^7$-Val-Leu-Gly$^{10}$-Lys-Leu-Ser-Gln-Glu-Leu-His-Lys(Fmoc)-Leu-Gln$^{20}$-Thr-Tyr-Pro-Arg-Thr-Asn-Thr-Gly-Ser-Gly$^{30}$-Thr-Pro-NH$_2$ (1,7-disulfide bond)(SEQ ID NO.: 1)

TABLE 20

| Materials | MW | eq | mmols | grams | ml |
|---|---|---|---|---|---|
| Deblocking | | | | | |
| Nsc-AA$^{sCt}$(11-32)-link-amide resin (above) | | 1.0 | 0.5 | 3.85 | — |
| DCM | | | | | 30 |
| 1% DBU-20% piperidine in DMF | | — | — | — | 40.0 |
| DMF(for each washing) | | — | — | — | 200 |
| Fragment condensation | | | | | |
| H-AAsCt(11-32)-link-amide resin (above) | — | 1.0 | 0.5 | — | — |
| Nsc-AAsCt (1-10)-OH (Example 13) | 1662 | 1.5 | 0.75 | 1.25 | — |
| DIPEA | 129.3 | 3.0 | 1.5 | 0.194 | 0.26 |
| Bop | 442.3 | 1.5 | 0.75 | 0.332 | — |
| HOBt | 135.1 | 1.5 | 0.80 | 0.108 | — |
| DMF | — | — | — | — | 4.0 |
| DCM | — | — | — | — | 16.0 |
| 1% DBU-20% piperidine in DMF | — | — | — | — | 20.0 |
| DMF(for each washing) | — | — | — | — | 20.0 |
| Introduction of DiFmoc | | | | | |
| 2% hydrazine hydrate in DMF | — | — | — | — | 60.0 |
| DMF | — | — | — | — | 240 |
| DCM | — | — | — | — | 160 |
| Fmoc-OSu | 337.3 | 5.0 | 10.0 | 3.37 | — |
| Cleavage | | | | | |
| TFA | — | — | — | — | 38 |
| TIS | — | — | — | — | 1.0 |
| water | — | — | — | — | 1.0 |
| diethyl ether | — | — | — | — | 500 |

Fragment condensation was conducted according to the method the same as that in Example 13 by using Nsc-AA$^{sCt}$(11-32)-link amide resin (3.85 g) prepared in the above and Nsc-AA$^{sCt}$(1-10)-OH (1.2 g) synthesized in Example 13 and the solvents and reagents shown in the above Table, and diFmoc was introduced by use of Fmoc-OSu to obtain 4.2 g of peptide attached resin. Peptide mixture obtained by reacting said peptide attached resin with TFA cleavage solution (2.5:2.5:95=TIS:water:TFA) was separated and purified to obtain 949 mg of 1,18-diFmoc salmon calcitonin.

Maldi Tof; 3877.41, (M+1=3877.44) HPLC; 98% up (peptide analysis condition 1)

EXAMPLE 16

Fragment condensation synthesis of 1,18-diNsc-salmon calcitonin using ivDde as a protecting group for branched amine of untargeted site Structure: Nsc-Cys[1]-Ser-Asn-Leu-Ser-Thr-Cys[7]-Val-Leu-Gly[10]-Lys-Leu-Ser-Gln-Glu-Leu-His-Lys(Nsc)-Leu-Gln[20]-Thr-Tyr-Pro-Arg-Thr-Asn-Thr-Gly-Ser-Gly[30]-Thr-Pro-NH$_2$ (SEQ ID NO.: 1)(1,7-disulfide bond)

TABLE 21

| Materials | MW | eq | mmols | grams | ml |
|---|---|---|---|---|---|
| Deblocking | | | | | |
| Nsc-AAsCt(11-32)-link-amide resin (Example 15) | — | 1.0 | 0.5 | 3.85 | — |
| DCM | | | | | 30 |
| 1% DBU-20% piperidine in DMF | — | — | — | — | 40.0 |
| DMF(for each washing) | — | — | — | — | 200 |
| Fragment condensation | | | | | |
| H-AAsCt(11-32)-link-amide resin (above) | — | 1.0 | 0.5 | — | — |
| Nsc-AAsCt(1-10)-OH (2.2) | 1662 | 1.5 | 0.75 | 1.25 | — |
| DIPEA | 129.3 | 3.0 | 1.5 | 0.194 | 0.26 |
| Bop | 442.3 | 1.5 | 0.75 | 0.332 | — |
| HOBt | 135.1 | 1.5 | 0.80 | 0.108 | — |
| DMF | — | — | — | — | 4.0 |
| DCM | — | — | — | — | 16.0 |
| 1% DBU-20% piperidine in DMF | — | — | — | — | 20.0 |
| DMF(for each washing) | — | — | — | — | 20.0 |
| Introduction of di-Nsc | | | | | |
| 2% hydrazine hydrate in DMF | — | — | — | — | 60.0 |
| DMF | — | — | — | — | 240 |
| DCM | — | — | — | — | 160 |
| Nsc-Osu | 372.3 | 5.0 | 10.0 | 3.72 | — |
| Cleavage (resin 1 g) | | | | | |
| TFA | — | — | — | — | 38 |
| TIS | — | — | — | — | 1.0 |
| water | — | — | — | — | 1.0 |
| diethyl ether | — | — | — | — | 500 |

Fragment condensation was conducted according to the method as in Example 13 by using Nsc-AA$^{sCt}$(11-32)-link amide resin(3.85 g) prepared in Example 15, Nsc-AA$^{sCt}$(1-10)-OH (1.2 g) prepared in Example 13 and the solvents and reagents shown in the above Table, and diNsc was introduced by use of Nsc-OSu (3.72 g in 20 ml DMF) to obtain 4.2 g of peptide attached resin. Peptide mixture obtained by reacting said peptide attached resin with TFA cleavage solution (2.5:2.5:95=TIS:water:TFA) was separated and purified to obtain 941 mg of 1,18-diNsc salmon calcitonin.

Maldi Tof; 3947.41, (M+1=3947.38) HPLC; 98% up (peptide analysis condition 1)

EXAMPLE 17

Fragment condensation synthesis of 11,18-diFmoc-salmon calcitonin using ivDde as a protecting group for branched amine of untargeted site

Example 17-1

Synthesis of 11-N$^\alpha$-Fmoc-11,18-di(ivDde)-AA$^{sCt}$ (11-32)-link amide resin Structure: Fmoc-Lys(ivDde)-Leu-Ser(tBu)-Gln(Trt)-Glu(tBu)-Leu-His(Trt)-Lys(ivDde)-Leu-Gln(Trt)-Thr(tBu)-Tyr(tBu)-Pro-Arg(Pbf)-Thr(tBu)-Asn(Trt)-Thr(tBu)-Gly-Ser(tBu)-Gly-Thr(tBu)-Pro-link amide resin(SEQ ID NO.: 4)

TABLE 22

| Materials | MW | eq | mmols | grams | ml |
|---|---|---|---|---|---|
| Chain assembly (per coupling cycle*) | | | | | |
| Link-amide resin | — | 1.0 | 1.0 | 2.0 | — |
| Nsc-amino acid* | — | 1.5 | 1.5 | — | — |
| Fmoc-Lys(ivDde)-OH × 2 | 574.6 | 1.5 | 1.5 | 0.861 | — |
| DIPEA* | 129.3 | 3.0 | 3.0 | 0.387 | 0.52 |
| Bop* | 442.3 | 1.5 | 1.5 | 0.442 | — |
| HOBt* | 135.1 | 1.5 | 1.5 | 0.135 | — |
| DMF* | — | — | — | — | 4.0 |
| DCM* | — | — | — | — | 16.0 |
| 1% DBU-20% piperidine in DMF* | — | — | — | — | 20.0 |
| DMF(for each washing)* | — | — | — | — | 20.0 |

Reaction order: Nsc-Pro, Nsc-Thr(tBu), Nsc-Gly, Nsc-Ser(tBu), Nsc-Gly, Nsc-Thr(tBu), Nsc-Asn(Trt), Nsc-Thr(tBu), Nsc-Arg(Pbf), Nsc-Pro, Nsc-Tyr(tBu), Nsc-Thr(tBu), Nsc-Gln(Trt), Nsc-Leu, Fmoc-Lys(ivDde), Nsc-His(Trt), Nsc-Leu, Nsc-Glu(tBu), Nsc-Gln(Trt), Nsc-Ser(tBu), Nsc-Leu, Fmoc-Lys(ivDde).

Synthesis was conducted according to the method as in Example 13, and as a result, well-dried resin 6.1 g was obtained, and peptide capacity of the resin was determined to be 0.15 mmol/g by UV spectrum analysis (UV-spectrum assay; capacity 0.15 mmol/g).

Example 17-2

Synthesis of 11,18-diFmoc-salmon calcitonin by condensation of Nsc-AA$^{sCt}$(1-10)-OH with Nsc-AA$^{sCt}$(11-32)-link amide resin Structure: H-Cys[1]-Ser-Asn-Leu-Ser-Thr-Cys[7]-Val-Leu-Gly[10]-Lys(Fmoc)-Leu-Ser-Gln-Glu-Leu-His-Lys(Fmoc)-Leu-Gln[20]-Thr-Tyr-Pro-Arg-Thr-Asn-Thr-Gly-Ser-Gly[30]-Thr-Pro-NH$_2$ (SEQ ID NO.: 1)(1,7-disulfide bond)

TABLE 23

| Materials | MW | eq | mmols | grams | ml |
|---|---|---|---|---|---|
| Deblocking | | | | | |
| Fmoc-AAsCt(11-32)-link-amide resin (above) | — | 1.0 | 0.5 | 3.33 | — |
| DCM | | | | | 30 |

TABLE 23-continued

| Materials | MW | eq | mmols | grams | ml |
|---|---|---|---|---|---|
| 1% DBU-20% piperidine in DMF | — | — | — | — | 40.0 |
| DMF(for each washing) | — | — | — | — | 180 |
| Fragment condensation | | | | | |
| H-AAsCt(11-32)-link-amide resin (above) | — | 1.0 | 0.5 | — | — |
| Nsc-AAsCt (1-10)-OH (Example 13) | 1662 | 1.5 | 0.75 | 1.25 | — |
| DIPEA | 129.3 | 3.0 | 1.5 | 0.194 | 0.26 |
| Bop | 442.3 | 1.5 | 0.75 | 0.332 | — |
| HOBt | 135.1 | 1.5 | 0.80 | 0.108 | — |
| DMF | — | — | — | — | 4.0 |
| DCM | — | — | — | — | 16.0 |
| 1% DBU-20% piperidine in DMF | — | — | — | — | 40.0 |
| DMF(for each washing) | — | — | — | — | 20.0 |
| Introduction of N-terminal Boc | | | | | |
| 1% DBU-20% piperidine in DMF | | | | | 40.0 |
| (Boc)2O | 218.3 | 5.0 | 2.5 | 0.55 | |
| DMF | | | | | 200 |
| Introduction of di-Fmoc | | | | | |
| 2% hydrazine hydrate in DMF | — | — | — | — | 60.0 |
| DMF | — | — | — | — | 240 |
| DCM | — | — | — | — | 160 |
| Fmoc-OSu | 337.3 | 5.0 | 10.0 | 3.37 | — |
| Cleavage (resin 1 g) | | | | | |
| TFA | — | — | — | — | 38 |
| TIS | | | | | 1.0 |
| water | | | | | 1.0 |
| diethyl ether | | | | | 500 |

Fragment condensation was conducted according to method as in Example 13 by using Fmoc-AA$^{sCt}$(11-32)-link amide resin (3.33 g) synthesized previously and Nsc-AA$^{sCt}$ (1-10)-OH (1.2 g) prepared in Example 13 and the solvents and reagents shown in the above Table. After the condensation, the removal of Nsc was performed by reacting with 2×20 ml deblocking solution (1% DBU-20% piperidine in DMF) for 5 min in each time, and washed with 4×20 ml DMF and reacted with excess amount of Boc$_2$O (0.55 g in 20 ml DMF) to protect N-terminal end with Boc, and washed with 5×20 ml DMF thoroughly. Then, the reaction product was treated with 2% hydrazine 3×20 ml for 10 to 30 min to remove base-labile ivDde, and the removal of ivDde was confirmed by TLC analysis based on comparison of the UV-absorbance between the reaction solution and 2% hydrazine. Upon completion of removal of ivDde, the resin was filtered and washed with 4×20 ml DMF, 4×20 ml DCM, 4×20 ml DMF, Fmoc-OSu (3.37 g in 20 ml DMF) was added and reacted for 2 hrs to introduce diFmoc. The introduction of diFmoc was checked by qualitative Kaiser test, the resin was washed with 4×20 ml DMF and 4×20 ml DCM, and dried under nitrogen to obtain 4.5 g of peptide attached resin.

Reaction solution obtained by reacting the resin obtained above with 40 ml of TFA-cleavage solution (2.5:2.5:95=TIS: water:TFA) at ordinary temperature for about 2 hrs, was filtered, added to 300 ml of cold ether to induce precipitation of peptide. The precipitate was separated by centrifuge, further washed with 2×100 ml of ether and dried to obtain 2.6 g of peptide mixture. The peptide mixture was purified by prep-HPLC, concentrated and subjected to lyophilization to obtain 769 mg of 11,18-diFmoc-salmon calcitonin.

Maldi Tof; 3877.41, (M+1=3877.44) HPLC; 98% up (peptide analysis condition 1)

EXAMPLE 18

Fragment condensation synthesis of 11,18-diNsc-salmon calcitonin using ivDde as a protecting group for branched amine of untargeted site Structure: H-Cys$^1$-Ser-Asn-Leu-Ser-Thr-Cys$^7$-Val-Leu-Gly$^{10}$-Lys(Nsc)-Leu-Ser-Gln-Glu-Leu-His-Lys(Nsc)-Leu-Gln$^{20}$-Thr-Tyr-Pro-Arg-Thr-Asn-Thr-Gly-Ser-Gly$^{30}$-Thr-Pro-NH$_2$ (SEQ ID NO.: 1)(1,7-disulfide bond)

TABLE 24

| Materials | MW | eq | mmols | grams | ml |
|---|---|---|---|---|---|
| Deblocking | | | | | |
| Fmoc-AAsCt(11-32)-link amide resin (Example 17) | — | 1.0 | 0.5 | 3.33 | — |
| DCM | | | | | 30 |
| 1% DBU-20% piperidine in DMF | — | — | — | — | 40.0 |
| DMF(for each washing) | — | — | — | — | 200 |
| Fragment condensation | | | | | |
| H-AAsCt(11-32)-link amide resin (above) | — | 1.0 | 0.5 | — | — |
| Nsc-AAsCt (1-10)-OH (Example 13) | 1662 | 1.5 | 0.75 | 1.25 | — |
| DIPEA | 129.3 | 3.0 | 1.5 | 0.194 | 0.26 |
| Bop | 442.3 | 1.5 | 0.75 | 0.332 | — |
| HOBt | 135.1 | 1.5 | 0.80 | 0.108 | — |
| DMF | — | — | — | — | 4.0 |
| DCM | — | — | — | — | 16.0 |
| 1% DBU-20% piperidine in DMF | — | — | — | — | 40.0 |
| DMF(for each washing) | — | — | — | — | 20.0 |
| Introduction of N-terminal Boc | | | | | |
| 1% DBU-20% piperidine in DMF | | | | | 40 |
| (Boc)2O | 218.3 | 5.0 | 2.5 | 0.55 | |
| DMF | | | | | 200 |
| Introduction of di-Nsc | | | | | |
| 2% hydrazine hydrate in DMF | — | — | — | — | 60.0 |
| DMF | — | — | — | — | 240 |
| DCM | — | — | — | — | 160 |
| Nsc-Osu | 372.3 | 5.0 | 10.0 | 3.72 | — |
| Cleavage (resin 1 g) | | | | | |
| TFA | — | — | — | — | 38 |
| TIS | | | | | 1.0 |
| water | | | | | 1.0 |
| diethyl ether | | | | | 500 |

Fragment condensation was conducted according to the method as in Example 13 by using Fmoc-AA$^{sCt}$(11-32)-link amide resin (3.33 g) synthesized in Example 17 and Nsc-AA$^{sCt}$(1-10)-OH (1.2 g) synthesized in Example 13 and the solvents and reagents shown in the above Table, and Boc (0.55 g in 20 ml DMF) was introduced as described in Example 17, ivDde was removed, and diNsc was introduced by use of Nsc-OSu (3.72 g in 20 ml DMF) to obtain 4.3 g of peptide attached resin. Peptide mixture obtained by reacting said peptide attached resin with TFA cleavage solution was separated and purified to obtain 942 mg of 11,18-diNsc-salmon calcitonin.

Maldi Tof; 3947.39, (M+1=3947.38) HPLC; 98% up (peptide analysis condition 1)

EXAMPLE 19

Fragment condensation synthesis of 1,12-diFmoc-GRF(1-29) using ivDde as a protecting group for branched amine of untargeted site

Example 19-1

Synthesis of Nsc-AA$^{GRF}$(1-15)-OH

Structure: Nsc-Tyr(tBu)-Ala-Asp(tBu)-Ala-Ile-Phe-Thr(tBu)-Asn(Trt)-Ser (Trt)-Tyr$^{10}$(tBu)-Arg(Pbf)-Lys(ivDde)-Val-Leu-Gly-OH (SEQ ID NO.: 5)

TABLE 25

| Materials | MW | eq | mmols | Grams | ml |
|---|---|---|---|---|---|
| Chain assembly (per coupling cycle*) | | | | | |
| Nsc-Gly-2-chlorotrityl resin | — | 1.0 | 5.0 | 8.2 | — |
| Nsc-†* | — | 1.5 | 7.5 | — | — |
| DIPEA* | 129.3 | 3.0 | 15.0 | 1.94 | 2.61 |
| Bop* | 442.3 | 1.5 | 7.5 | 3.32 | — |
| HOBt* | 135.1 | 1.5 | 7.5 | 1.01 | — |
| DMF* | — | — | — | — | 4.0 |
| DCM* | — | — | — | — | 16.0 |
| 1% DBU-20% piperidine in DMF* | — | — | — | — | 100 |
| DMF(for each washing)* | — | — | — | — | 50.0 |
| Cleavage | | | | | |
| TFE | — | — | — | — | 10 |
| AcOH | — | — | — | — | 10 |
| DCM | — | — | — | — | 280 |
| Ethanol | — | — | — | — | 100 |
| Water | — | — | — | — | 100 |

Reaction order: Nsc-Leu, Nsc-Val, Fmoc-Lys(ivDde), Nsc-Arg(Pbf), Nsc-Tyr(tBu), Nsc-Ser(Trt), Nsc-Asn(Trt), Nsc-Thr(tBu), Nsc-Phe, Nsc-Ile, Nsc-Ala, Nsc-Asp(tBu), Nsc-Ala, Nsc-Tyr(tBu)

Nsc-Gly-2-CLTR synthesized as in Example 13 was put in 200 ml peptide reactor, 50 ml DCM was poured and left to allow the resin to sufficiently expand. DCM was removed by filtration and it was treated with 2×50 ml deblocking solution (1% DBU-20% piperidine in DMF) for 5 min in each time to remove Nsc. Then, for the next reaction, the resulting mixture was washed 5-7 times well with DMF. Coupling reaction was conducted as described in Example 1 according to the reaction order indicated above by using Nsc- or Fmoc-protected amino acid (1.5 eq), HOBt(1.5 eq), Bop(1.5 eq) and DIPEA (3.0 eq). The reaction was checked by Kaiser test and the presence of amine in the washing solution was confirmed by chloranil test.

Thus obtained peptide attached resin was treated for 3 hrs at condition under which the peptide could be separated from 2-CTRL resin with other protecting group being maintained, that is, 100 ml DCM:TFE:AcOH (8:1:1), the reaction solution was then separated by filtration and the resin was washed with 2×100 ml DCM. The reaction solution and the washings were collected and concentrated to ¼ volume, diluted with 100 ml ethanol and 100 ml water and left in a refrigerator for 12 hrs. Solid thus formed was filtered and dried to obtain 12.6 g of Nsc-AA$^{GRF}$(1-15)-OH.

Maldi Tof; 3144.09, (M+1=3143.95) HPLC; 92% up (peptide analysis condition 2)

Example 19-2

Synthesis of Nsc-AA$^{GRF}$(16-29)-link amide resin

Structure: Nsc-Gln(Trt)-Leu-Ser(Trt)-Ala-Arg(Pbf)-Lys(Boc)-Leu-Leu-Gln(Trt)-Asp(tBu)-Ile-Met-Ser(Trt)-Arg(Pbf)-link amide resin(SEQ ID NO.: 6)

TABLE 26

| Materials | MW | eq | mmols | grams | ml |
|---|---|---|---|---|---|
| Chain assembly (per coupling cycle*) | | | | | |
| Link-amide resin | — | 1.0 | 1.0 | 2.0 | — |
| Nsc-amino acid* | — | 1.5 | 1.5 | — | — |
| Fmoc-Lys(ivDde)-OH | 574.6 | 1.5 | 1.5 | 0.861 | — |
| DIPEA* | 129.3 | 3.0 | 3.0 | 0.387 | 0.52 |
| Bop* | 442.3 | 1.5 | 1.5 | 0.442 | — |
| HOBt* | 135.1 | 1.5 | 1.5 | 0.135 | — |
| DMF* | — | — | — | — | 4.0 |
| DCM* | — | — | — | — | 16.0 |
| 1% DBU-20% piperidine in DMF* | — | — | — | — | 40.0 |
| DMF(for each washing)* | — | — | — | — | 20.0 |

Reaction order: Nsc-Arg(pbf), Nsc-Ser(Trt), Nsc-Met, Nsc-Ile, Nsc-Asp(tBu), Nsc-Gln(Trt), Nsc-Leu, Nsc-Leu, Nsc-Lys(Boc), Nsc-Arg(Pbf), Nsc-Ala, Nsc-Ser(Trt), Nsc-Leu, Nsc-Gln(Trt)

Coupling and deblocking were conducted as described in Example 1 according to the indicated reaction order by using link amide resin 2.0 g and reagents and solvents listed in the above Table. The coupling was checked by Kaiser test, and removal of side reactants remaining in the washing was confirmed by chloranil test. Peptide attached resin finally obtained was 6.5 g, and reaction capacity was determined to be 0.12 mmol/g based on UV-assay.

Example 19-3

Synthesis of 1,12-diFmoc-GRF(1-29) by condensation of Nsc-AA$^{GRF}$(1-15)-OH with Nsc-AA$^{GRF}$(16-29)-link amide resin Structure: Fmoc-Tyr-Ala-Asp-Ala-Ile-Phe-Thr-Asn-Ser-Tyr$^{10}$-Arg-Lys Fmoc)-Val-Leu-Gly-Gln-Leu-Ser-Ala-Arg$^{20}$-Lys-Leu-Leu-Gln-Asp-Ile-Met-Ser-Arg-NH$_2$(SEQ ID NO.: 2)

TABLE 27

| Materials | MW | eq | mmols | grams | ml |
|---|---|---|---|---|---|
| Deblocking | | | | | |
| Nsc-AAGRF(16-29)-link amide resin (above) | — | 1.0 | 0.5 | 4.17 | — |
| DCM | | | | | 30 |
| 1% DBU-20% piperidine in DMF | — | — | — | — | 40.0 |
| DMF(for each washing) | — | — | — | — | 200 |
| Fragment condensation | | | | | |
| H-AAGRF(16-29)-link amide resin (above) | — | 1.0 | 0.5 | — | — |
| Nsc-AAGRF(1-15)-OH (above) | 3143 | 1.5 | 0.75 | 2.36 | — |
| DIPEA | 129.3 | 3.0 | 1.5 | 0.194 | 0.26 |
| Bop | 442.3 | 1.5 | 0.75 | 0.332 | — |

TABLE 27-continued

| Materials | MW | eq | mmols | grams | ml |
|---|---|---|---|---|---|
| HOBt | 135.1 | 1.5 | 0.80 | 0.108 | — |
| DMSO | — | — | — | — | 10 |
| DCM | — | — | — | — | 16.0 |
| 1% DBU-20% piperidine in DMF | — | — | — | — | 20.0 |
| DMF(for each washing) | — | — | — | — | 20.0 |
| Introduction of di-Fmoc | | | | | |
| 2% hydrazine hydrate in DMF | — | — | — | — | 60.0 |
| DMF | — | — | — | — | 240 |
| DCM | — | — | — | — | 160 |
| Fmoc-OSu | 337.3 | 5.0 | 10.0 | 3.37 | — |
| Cleavage (resin 1 g) | | | | | |
| TFA | — | — | — | — | 11.5 |
| TIS | — | — | — | — | 0.25 |
| water | — | — | — | — | 0.25 |
| diethyl ether | — | — | — | — | 400 |

Nsc-AA$^{GRF}$(16-29)-link amide resin(4.17 g) synthesized as above was placed on an adequate peptide reactor. To the reactor, 30 ml DCM was poured to allow the resin to sufficiently expand, and the solution was removed via filtration, treated with 2×20 ml deblocking solution (1% DBU-20% piperidine in DMF) for 5 min in each time to remove Nsc. The resin was washed thoroughly with DMF, and Nsc-AA$^{GRF}$(1-15)-OH (2.36 g) prepared previously was put to the reactor by dissolving in 10 ml DMSO. HOBt, DIPEA, Bop etc., listed in the above Table were added to the reaction solution and reacted for 12 hrs. Progress of reaction was checked by HPLC every 2 hrs and when confirmed to be completed, the reaction solution was thoroughly washed with DMF.

After fragment condensation was completed, the resin was treated with 2% hydrazine in DMF (3×20 ml) for 20 min in each time to remove ivDde and Nsc. The removal of ivDde was confirmed by TLC analysis as described in Example 4, and the resulting product was thoroughly washed with washing solvent. Fmoc was introduced to 1,12-positions by treating with Fmoc-OSu(3.37 g in 20 ml DMF) for 2 hrs, the resin was washed well, subjected to vacuum dry to obtain 4.3 g of peptide attached resin.

1 g of said dried resin was withdrawn and reacted with 10 ml cleavage solution (2.5:2.5:95=TIS:water:TFA) at ordinary temperature for about 90 min and further reacted with TMS-Br and EDT for 15 min. Resin was removed via filtration and the resin was washed with 2 ml TFA. The washing and filtrate were collected, added to 100 ml ether and subjected to centrifuge to allow formed precipitate to be precipitated, and additionally centrifuged and washed with 3×50 ml ether. The precipitate was dried with nitrogen to obtain 654 mg of dried peptide mixture, and this mixture was purified with prep-HPLC, lyophilized to obtain 141 mg of 1,12-diFmoc-GRF(1-29).

Maldi Tof; 3803.49, (M+1=3803.46) HPLC; 97% up (peptide analysis condition 1)

EXAMPLE 20

Preparation of Lys$^{18}$-PEG 2K-salmon calcitonin using 1,11-diFmoc salmon calcitonin 1,11-diFmoc salmon calcitonin 10 mg eq was dissolved in DMF 1 ml, and after 0.2% TEA was added and poly(ethyleneglycol) 2,000 succinimidyl propionate 5 eq was added and reacted at 45° C. for 1 hr. Piperidine 50 μl was added and reacted for 5 min to remove Fmoc, and then acidified by addition of 10% trifluoroacetic acid/acetonitrile 500 μl. This reaction solution was diluted 10 times with 20 mM sodium acetate buffer (pH 4.5) and purified by ionic exchange chromatography under the following condition. Effluent was added and allowed to adhere to C-18 Sep-Pak catridge, washed with 20 ml distilled water, and eluted with 5 ml of 70% acetonitrile. Acetonitrile in the effluent was evaporated under nitrogen and subjected to lyophilization.

Figure 2:
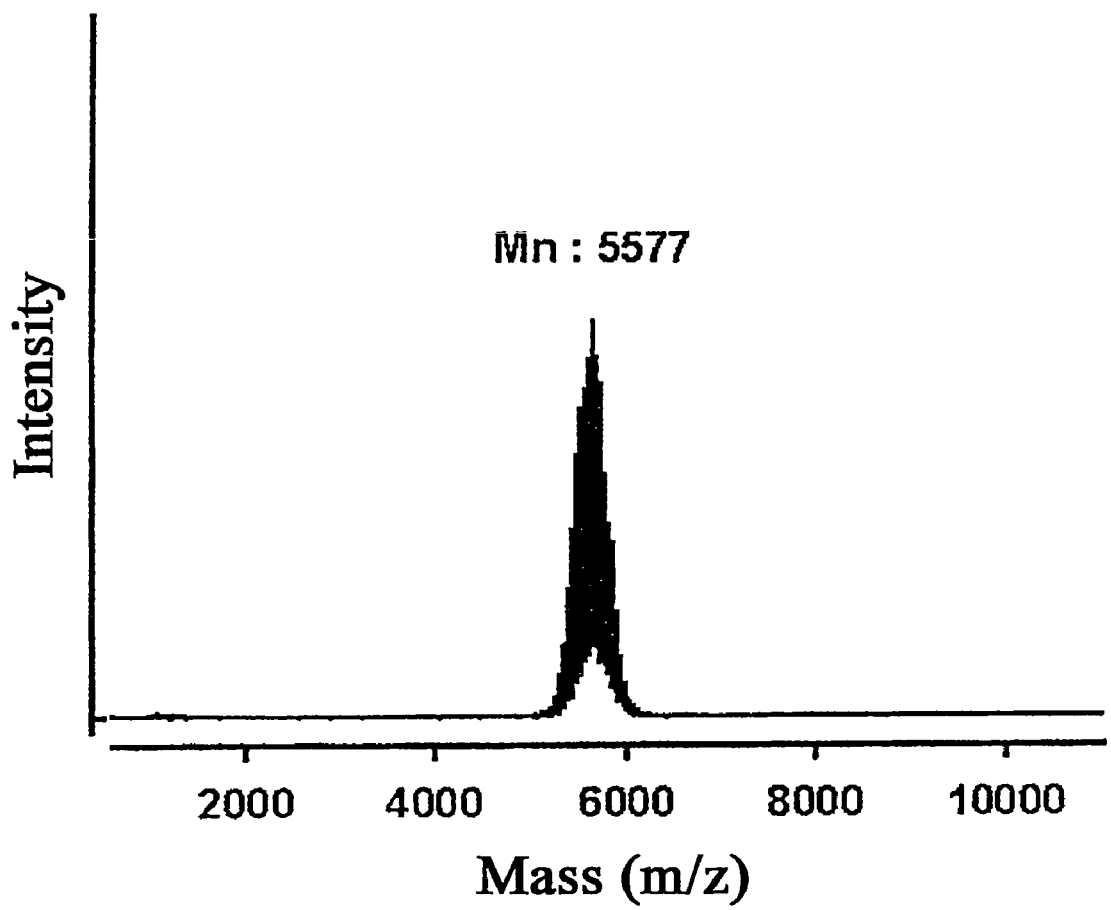
FIG. 2 shows MALDI-TOF mass spectra for Lys-C enzyme-treated fragments of salmon calcitonin(A) and $Lys^{18}$-PEG 2K-salmon calcitonin in Example 20(B).
Figure 3:
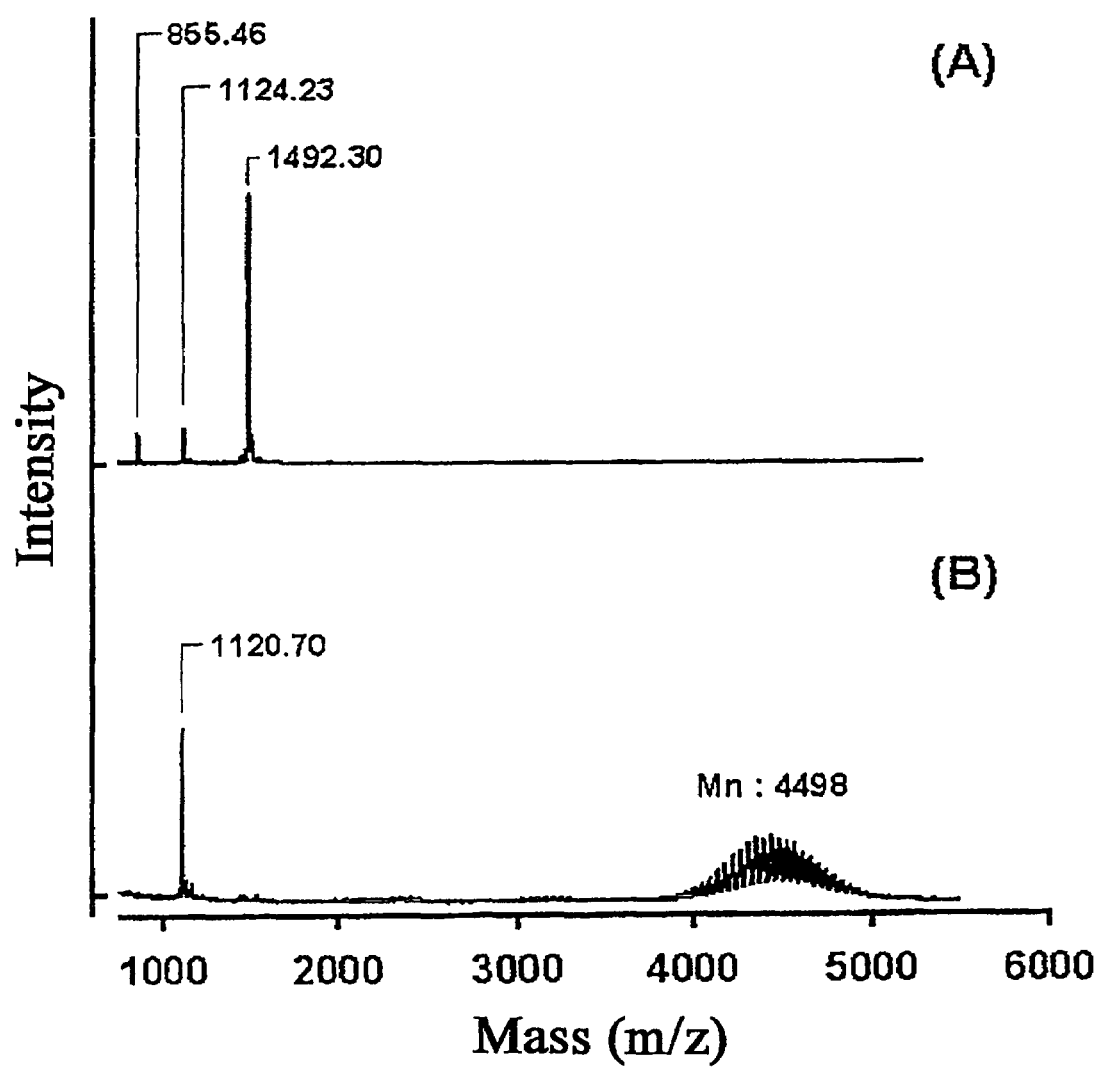
FIG. 3 represents MALDI-TOF mass spectra for salmon calcitonin(A) and $Lys^{18}$-PEG 2K-salmon calcitonin in Example 20(B).

When determined as described in Experimental Example 1, reverse phase chromatogram of said sample (FIG. 1-B) showed a single peak, and unreacted salmon calcitonin, di-PEG 2K-salmon calcitonin, tri-PEG 2K salmon calcitonin etc., besides mono-PEG 2K salmon calcitonin were not identified by MALDI-TOF mass spectrum (FIG. 2). In addition, MALDI-TOF mass spectrum for Lys-C enzyme treated fragment measured as described in Experimental Example 1 was exhibited only the peak corresponding to the fragment, Lys$^{18}$-PEG 2K-GRF(1-29) (FIG. 3-B). When the sample was dissolved in distilled water and determined against salmon calcitonin standard based on reverse phase chromatography as described in Experimental Example 1, yield was 87.6%.

[Ionic Exchange Chromatography Condition]
Column: TSK SP-5PW (55×200 mm, 15 μm)(strong cation-exchange media)
Eluent
Eluent A: 20 mM sodium acetate(pH 4.5)
Eluent B: 300 mM sodium chloride/20 mM sodium acetate (pH 4.5)
Eluent C: 1 M sodium chloride/20 mM sodium acetate(pH 4.5)
00-10 min: 100% A
10-40 min: 0% A→100% B
40-50 min: 100% C
Flow rate: 3 ml/min
Detection: UV 215 nm

COMPARATIVE EXAMPLE 1

Preparation of mono-PEG 2K-salmon calcitonin using salmon calcitonin

Salmon calcitonin 10 mg was dissolved in 5 ml of 10 mM sodium phosphate buffer (pH 7.5) and poly(ethyleneglycol) 2,000 succinimidyl propionate 1.5 eq was added and reacted at ordinary temperature for 20 min, and then 1M glycine solution 50 μl was added and left for 30 min to complete the reaction. The reaction solution was divided in 5 parts by using size-exclusion chromatography to separate mono-PEG conjugate. The effluent was collected and allowed to adhere to C-18 Sep-Pak catridge, washed with 20 ml of distilled water and eluted with 5 ml of 70% acetonitrile. Acetonitrile in the effluent was evaporated under nitrogen stream and lyophilized.

When determined as described in Experimental Example 1, reverse phase chromatogram of this sample showed three peaks indicating Cys$^1$-N$^α$-PEG 2K-salmon calcitonin, Lys$^{11}$-PEG 2K-salmon calcitonin and Lys$^{18}$-PEG 2K-salmon calcitonin (FIG. 1-A) and the ratio of peak area was approximately 1:1:1. The sample was dissolved in distilled water and determined based on reverse phase chromatogram as described in Experimental Example 1 against salmon calcitonin standard to obtain yield of 28.4%.

[Size-Exclusion Chromatography Condition]
Column: Superose 12 HR 10/30 (Amersham pharmacia)
Eluent: 10 mM PBS (pH 7.4)
Flow rate: 0.4 ml/min
Detection: UV 215 nm

EXPERIMENTAL EXAMPLE 1

Identification of Lys[18]-PEG 2K-salmon calcitonin

Experimental Example 1-1

Identification and determination of isomers based on reverse phase chromatography Samples obtained in Example 20 and Comparative Example 1 were compared by reverse phase chromatography under the following condition according to the method described in Pharm. Res., 16(6), 813-818, 1999. While the sample in Example 20 exhibited a single peak indicating Lys[18]-PEG 2K-salmon calcitonin (FIG. 1-B), the sample in Comparative Example 1 showed peaks corresponding to Cys[1]-N$^\alpha$-PEG 2K-salmon calcitonin, Lys[11]-PEG 2K-salmon calcitonin and Lys [18]-PEG 2K-salmon calcitonin in a ratio of 1:1:1 (FIG. 1-A). Yield of Example 20 was 87.6% when calculated into ratio of peak area of Lys[18]-PEG 2K-salmon calcitonin to that of salmon calcitonin standard. In Comparative Example 1, the overall yield for mono-PEG conjugate was 28.4%, when calculated based on the ratio of total peak area of the three positional isomers against that of salmon calcitonin standard, and yield for Lys[18]-PEG 2K-salmon calcitonin (peak 2) was 10.2%.

[Reverse Phase Chromatography Condition]
Column: Lichrospher100 RP-8 (4 mm ID×250 mm L, 5 μm, Merck)
Mobile phase
Eluent A: 0.1% TFA/D.W.
Eluent B: 0.1% TFA/AcCN
00-30 min: 36% B→44% B
Flow rate: 1 ml/min
Detection: UV 215 nm Experimental Example 1-2

Identification of side reactants and isomers by MALDI-TOF mass analysis

The sample of Example 20, when analyzed under the following MALDI-TOF mass analysis condition, showed the only peak corresponding to mono-PEG 2K-salmon calcitonin, and unreacted salmon calcitonin, di-PEG 2K-salmon calcitonin, tri-PEG 2K-salmon calcitonin etc., were not exhibited (FIG. 2). MALDI-TOF mass spectrum for peptide fragment obtained by treating the sample from the Example 20 with Lys-C enzyme was shown in FIG. 3 in comparison with salmon calcitonin standard which was treated identically. The Lys-C enzyme-treated sample was prepared by reacting the sample 10 μl with 5 μl of 50 mM tris buffer (pH 8.5) containing Lys-C enzyme (0.1 μg/ml) for 1 hr at 37° C. and by mixing with matrix solution in a ratio of 1:2. MALDI-TOF mass spectrum for Lys-C enzyme treated fragment of salmon calcitonin (FIG. 3-A) confirmed peaks corresponding to Pro[1]-Gly[10] fragment, Lys[11]-His[17] fragment and Lys[18]-pro[32] fragment, yet the MALDI-TOF mass spectrum for Lys-C enzyme treated fragment of Example 20 sample (FIG. 3-B) exhibited only the peaks corresponding to Pro[1]-Gly[10] fragment and PEG-attached Lys[11]-pro[32] fragment, and peaks for Lys[11]-His[17] fragment and Lys[18]-pro[32] fragment were not detected. Based on this result, it could be confirmed that the sample of Example 20 is Lys[18]-mono-PEG 2K-salmon calcitonin where PEG is combined to only Lys[18] position.

[MALDI-TGF Mass Analysis Condition]
Ion selection: positive ion
Matrix solution: α-cyano-4-hydroxy cinnamic acid saturated solution (0.1% TFA/50% AcCN/DW)
Mode: linear
Sample: matrix=1:2
Accelerating voltage: 25 kV

EXAMPLE 21

Preparation of Lys[18]-PEG 1K-salmon calcitonin, Lys[18]-PEG 5K-salmon calcitonin, and Lys[18]-PEG 10K-salmon calcitonin using 1,11-diFmoc-salmon calcitonin According to the method as described in Example 20, Lys[18]-PEG 1K-salmon calcitonin, Lys[18]-PEG 5K-salmon calcitonin, and Lys[18]-PEG 10K-salmon calcitonin were prepared, respectively, by using 1,11-diFmoc-salmon calcitonin and poly(etyhyleneglycol) 1,000 succinimidyl propionate, poly(ethyleneglycol) 5,000 succinimidyl propionante and poly(ethyleneglycol) 10,000 succinimidyl propionate. When individual samples were determined by the procedure described in Example 1, the yield was 86.9%, 81.5% and 82.7%, respectively, and no other peptide-derived substance or isomer except Lys[18]-PEG conjugate was identified.

EXAMPLE 22

Preparation of Lys[18]-PEG 2K-salmon calcitonin using 1,11-diNsc-salmon calcitonin 1,11-diNsc salmon calcitonin 10 mg eq was dissolved in 1 ml DMF and 0.2% TEA was added, and then poly(ethyleneglycol) 2,000 succinimidyl propionate 5 eq was added and reaction was conducted for 1 hr at 45° C. Piperidine 100 μl was added and reacted for 5 min to remove Nsc, and then acidified by 500 μl of 10% trifluoroacetic acid/acetonitrile. This reaction solution was purified under the same condition as in Example 20, and weighted against salmon calcitonin with the method of Experimental Example 1 to obtain yield of 84.8%. Additionally, in case of both reverse phase chromatogram and MALDI-TOF mass spectrum for Lys-C enzyme treated fragment obtained as described in Experimental Example 1, no peptide-derived substance or isomer except Lys[18]-PEG 2K-salmon calcitonin was identified.

EXAMPLE 23

Preparation of Lys[21]-PEG 5K-GRF(1-29) using 1,12-diFmoc-GRF(1-29)

Figure 4:
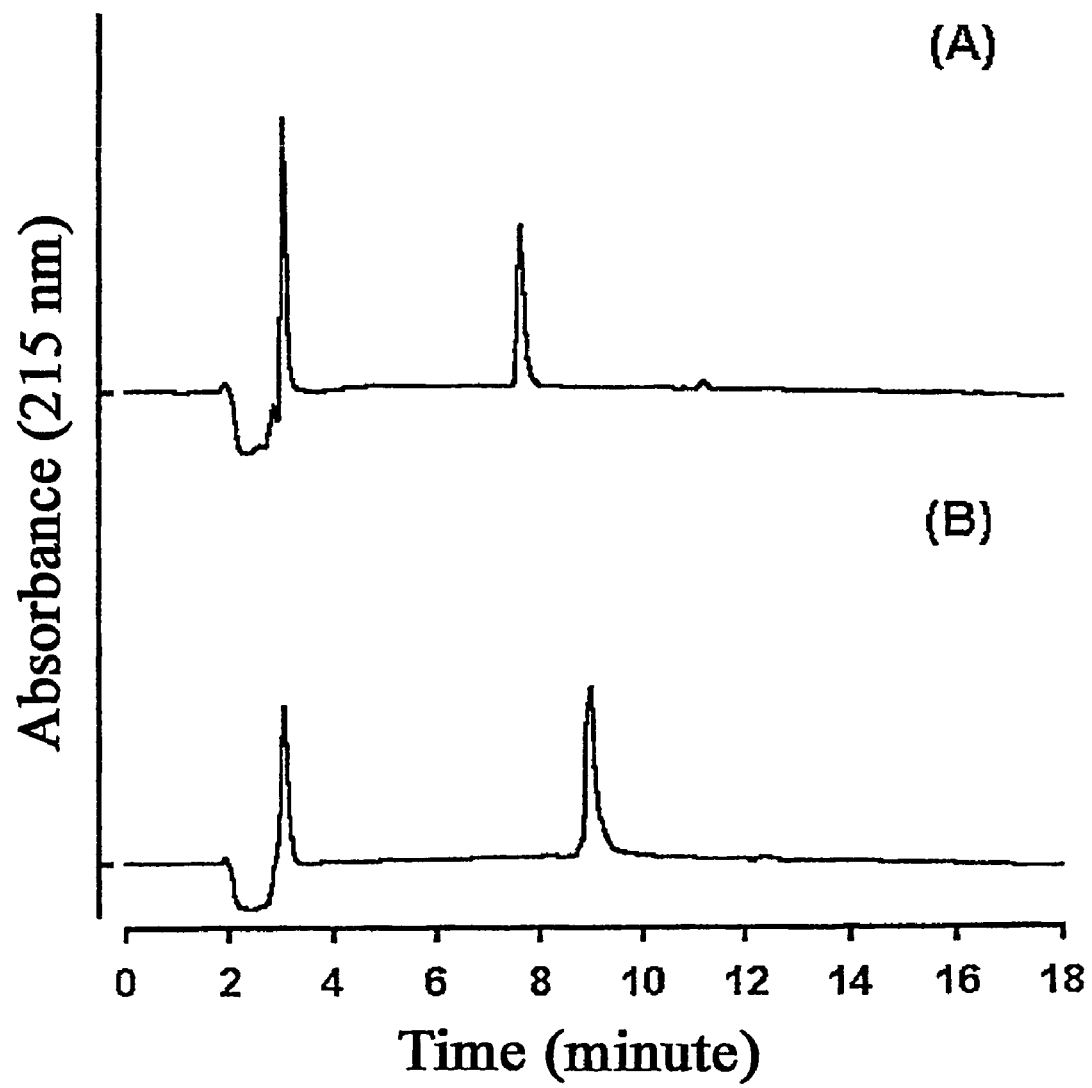
FIG. 4 shows reverse phase chromatograms for GRF(1-29) (A) and $Lys^{21}$-PEG 5K-GRF(1-29) in Example 23(B).
Figure 5:
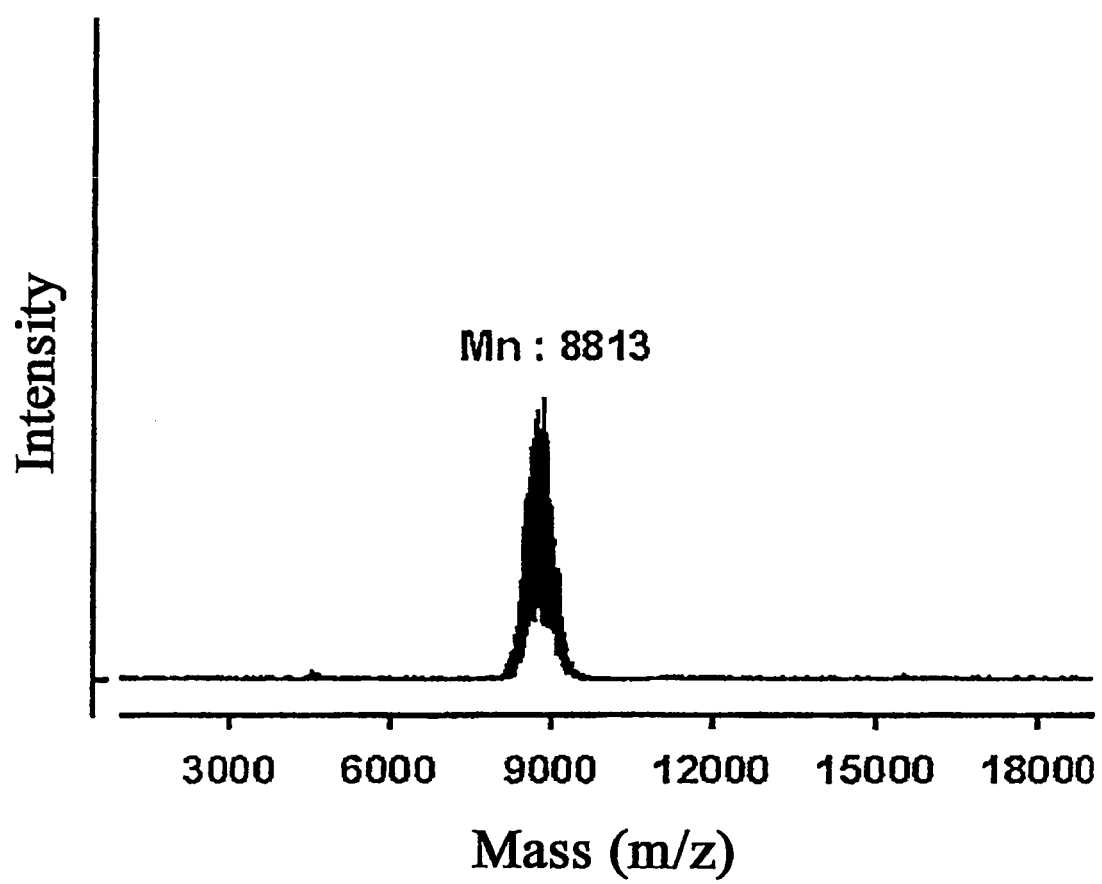
FIG. 5 represents MALDI-TOF mass spectrum for $Lys^{21}$-PEG 5K-GRF(1-29) in Example 23.
Figure 6:
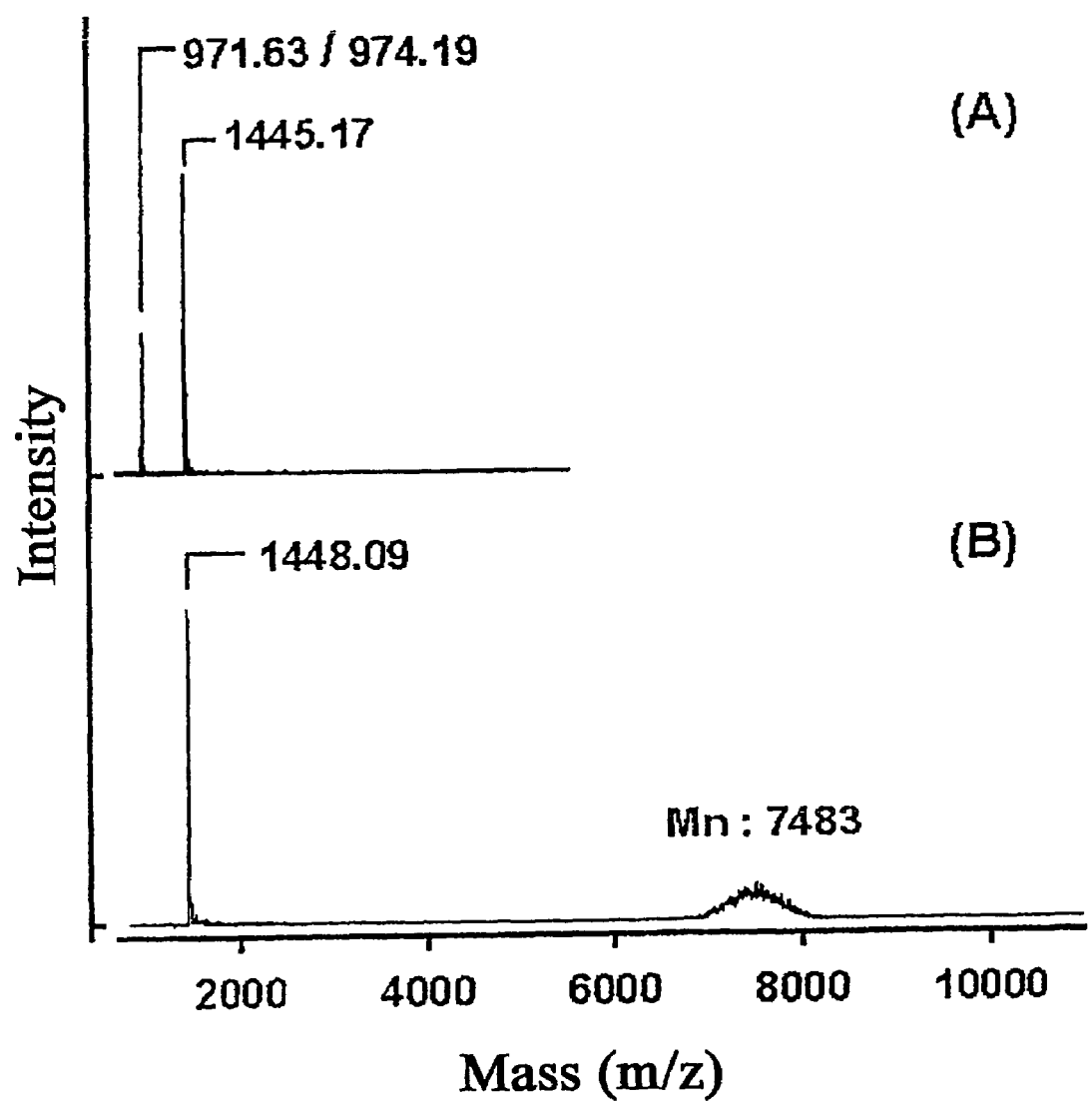
FIG. 6 represents MALDI-TOF mass spectra Lys-C enzyme-treated fragments of GRF(1-29)(A) and of $Lys^{21}$-PEG 5K-GRF(1-29) (B) in Example 23.

1,12-diFmoc-GRF(1-29) 10 mg eq was dissolved in DMF 1 ml and 0.2% TEA was added, and then poly(ethyleneglycol) 5,000 succinimidyl propionate 5 eq was added and reaction was conducted at 45° C. for 1 hr. Piperidine 50 μl was added and reacted for 5 min to remove Fmoc, and then acidified by 500 μl of 10% trifluoroacetic acid/acetonitrile. This reaction solution was purified by the same method as in Example 20 to obtain PEG conjugated peptide. When this sample was determined as described in Experimental Example 2, reverse phase chromatogram of the sample (FIG. 4-B) exhibited a single peak, and MALDI-TOF mass spectrum thereof also exhibited only the peak corresponding to mono-PEG 5K-GRF(1-29) and unreacted GRF(1-29), di-PEG 5K-GRF(1-29) and tri-PEG 5K-GRF(1-29) were not identified (FIG. 5). In addition, MALDI-TOF mass spectrum for Lys-C enzyme treated fragment, which was obtained as described in Experimental Example 2, showed only the peak corresponding to Lys[21]-PEG 5K-GRF(1-29) fragment (FIG. 6-B). When the sample was dissolved in distilled water and subjected to analysis based on reverse phase chromatography as described in Experimental Example 2 against GRF(1-29) standard, the yield was 91.2%.

EXPERIMENTAL EXAMPLE 2

Identification of Lys$^{21}$-PEG 5K-GRF(1-29)

According to reverse phase chromatogram obtained under the following condition, the sample of Example 23 showed a single peak corresponding to mono-PEG 5K-GRF(1-29) (FIG. 4-B), and did not exhibit the peak corresponding to unreacted GRF(1-29) (FIG. 4-A) or other peak. In addition, MALDI-TOF mass spectrum obtained by the method as in Experimental Example 1 did not exhibit other peptide-derived peaks except mono-PEG 5K-GRF(1-29) (FIG. 5). Further, MALDI-TOF mass spectrum for Lys-C enzyme treated fragment obtained by the method as in Experimental Example 1(FIG. 6-B) also exhibited only the peaks for Try$^1$~Arg$^{11}$ fragment and Lys$^{12}$~Arg$^{29}$ fragment to which PEG 5K was combined, yet the peaks for Lys$^{12}$~Arg$^{20}$ fragment or Lys$^{21}$~Arg$^{29}$ fragment which were identified in MALDI-TOF mass spectrum obtained for GRF(1-29) identically treated (FIG. 6-A), were not identified. Based on this result, it could be confirmed that the sample of Example 23 is Lys$^{21}$-mono-PEG 5K-GRF(1-29) in which PEG is combined to only Lys$^{21}$ position.

[Reverse Phase Chromatography Condition]

Column: Lichrospher100 RP-8 (4 mm ID×250 mm L, 5 μm, Merck)

Mobile phase

Eluent A; 0.1% TFA/D.W.

Eluent B; 0.1% TFA/AcCN 00-15 min: 34% B→55% B

Flow rate: 1 ml/min

Detection: UV 215 nm

EXAMPLE 24

Preparation of Lys$^{21}$-PEG 1K-GRF(1-29) using 1,12-diNsc-GRF(1-29)

1,12-diNsc-GRF(1-29) 10 mg eq was dissolved in 1 ml of DMF and 0.2% TEA was added, then poly(ethyleneglycol) 1,000 succinimidyl propionate 5 eq was added and reaction was conducted at 45° C. for 1 hr. Piperidine 100 μl was added and reacted for 5 min to remove Nsc, and then acidified by 10% trifluoroacetic acid/acetonitrile 500 μl. This reaction solution was purified under the same condition as in Example 20, and then subjected to analysis by reverse phase chromatography as described in Experimental Example 2 against GRF(1-29) standard to obtain yield of 92.8%. In addition, MALDI-TOF mass spectrum obtained as described in Experimental Example 1 showed only the peak corresponding to mono-PEG 1K-GRF(1-29), and MALDI-TOF mass spectrum for Lys-C enzyme treated fragment also showed only the peak corresponding to Lys$^{21}$-PEG 1K-GRF(1-29) fragment.

INDUSTRIAL APPLICABILITY

The present invention enables synthesis of peptides having selectively protected amine of untargeted sites simply by changing acid-base conditions. Accordingly, when compared to conventional methods for the production of PEG conjugated peptides in which PEG is specifically combined to amine of targeted site, the present invention has following advantages; the final products can be obtained with much higher yield, complicated separation and purification is not necessary, thus the present invention provide economical methods, and formation of side products inevitably accompanied by the conventional process is inhibited, thus, the product according to the present invention is more adequate for clinical use. Therefore, when the PEG conjugated peptide of the present invention is used for clinical use, PEGylation effect can be maximized.

The invention claimed is:

1. A method for preparing a peptide having selectively protected amines of untargeted sites comprising synthesizing the peptide by separately blocking amines of targeted sites of the peptide with either ivDde or Mtt, and amines of untargeted sites of the peptide with Boc, and protecting $N^{\alpha}$-amine of the peptide with Fmoc or Nsc, wherein the peptide contains at least one targeted site and at least one untargeted site.

2. The method of claim 1, further comprising substituting the amine protecting groups for amines of the untargeted sites and for the $N^{\alpha}$-amine with at least one final amine protecting group selected from the group consisting of Fmoc, Nsc, Dde and ivDde.

3. The method of claim 1, further comprising substituting the amine protecting groups for amines of the untargeted sites and for the $N^{\alpha}$-amine with Boc.

4. The method of claim 1, wherein synthesis of the peptide is performed by solid phase synthesis.

5. The method of claim 1, wherein the peptide is divided into at least two fragments, the fragments are synthesized separately, and then the fragments are condensed to form the peptide.

6. A method for preparing a peptide having selectively protected sites comprising synthesizing the peptide by separately blocking amines of polyethylene glycol (PEG)-targeted sites of the peptide with Boc, and amines of untargeted sites of the peptide with either ivDde or Mtt, and protecting $N^{\alpha}$-amine of the peptide with Fmoc or Nsc, wherein the PEG-targeted sites are sites to be conjugated with polyethylene glycol (PEG) and the untargeted sites are to remain as free amine after conjugating targeted sites with PEG, wherein the peptide has at least one targeted site and at least one untargeted site.

7. A method for preparing a peptide for conjugation of PEG at selected sites, the method comprising synthesizing the peptide by separately blocking amines of polyethylene glycol (PEG)-targeted sites of the peptide with either ivDde or Mtt, and amines of untargeted sites of the peptide with Boc, and protecting $N^{\alpha}$-amine of the peptides with Fmoc or Nsc, wherein the peptide has at least one targeted site and at least one untargeted site and following synthesis of the peptides, the targeted sites are conjugated with polyethylene glycol (PEG) and the untargeted sites remain as free amine after conjugating targeted sites with PEG.

* * * * *

SEQUENCE LISTING

```
<160> NUMBER OF SEQ ID NOS: 6

<210> SEQ ID NO 1
<211> LENGTH: 32
<212> TYPE: PRT
<213> ORGANISM: Oncorhynchus keta
<220> FEATURE:
<221> NAME/KEY: DISULFID
<222> LOCATION: 1..7
<223> OTHER INFORMATION: disulfide bond
<300> PUBLICATION INFORMATION:
<301> AUTHORS: O'Dor, RK
         Parkes, CO
         Copp, DH
<302> TITLE: Amino acid composition of salmon calcitonin
<303> JOURNAL: Can. J. Biochem.
<305> ISSUE: 47
<306> PAGES: 823-825
<307> DATE: 1969-01-01

<400> SEQUENCE: 1

Cys Ser Asn Leu Ser Thr Cys Val Leu Gly Lys Leu Ser Gln Glu Leu
 1               5                  10                  15

His Lys Leu Gln Thr Tyr Pro Arg Thr Asn Thr Gly Ser Gly Thr Pro
            20                  25                  30
```

```
<210> SEQ ID NO 2
<211> LENGTH: 29
<212> TYPE: PRT
<213> ORGANISM: Homo sapiens
<300> PUBLICATION INFORMATION:
<301> AUTHORS: Rivier, J. et al.
<302> TITLE: Characterization of a growth hormone-releasing factor from
      a human pancreatic islet tumor
<303> JOURNAL: Nature
<305> ISSUE: 300
<306> PAGES: 276-278
<307> DATE: 1982-01-01

<400> SEQUENCE: 2

Tyr Ala Asp Ala Ile Phe Thr Asn Ser Tyr Arg Lys Val Leu Gly Gln
 1               5                  10                  15

Leu Ser Ala Arg Lys Leu Leu Gln Asp Ile Met Ser Arg
            20                  25

<210> SEQ ID NO 3
<211> LENGTH: 10
<212> TYPE: PRT
<213> ORGANISM: artificial
<220> FEATURE:
<221> NAME/KEY: DISULFID
<222> LOCATION: 1..7
<223> OTHER INFORMATION: chemically synthesized peptide

<400> SEQUENCE: 3

Cys Ser Asn Leu Ser Thr Cys Val Leu Gly
 1               5                  10

<210> SEQ ID NO 4
<211> LENGTH: 22
<212> TYPE: PRT
<213> ORGANISM: artificial
<220> FEATURE:
<221> NAME/KEY:
<222> LOCATION: 1..22
<223> OTHER INFORMATION: chemically synthesized peptide

<400> SEQUENCE: 4

Lys Leu Ser Gln Glu Leu His Lys Leu Gln Thr Tyr Pro Arg Thr Asn
 1               5                  10                  15

Thr Gly Ser Gly Thr Pro
            20

<210> SEQ ID NO 5
<211> LENGTH: 15
<212> TYPE: PRT
<213> ORGANISM: artificial
<220> FEATURE:
<221> NAME/KEY:
<222> LOCATION: 1..15
<223> OTHER INFORMATION: chemically synthesized peptide corresponding to
      amino acids 1-15 of SEQ ID NO. 2

<400> SEQUENCE: 5

Tyr Ala Asp Ala Ile Phe Thr Asn Ser Tyr Arg Lys Val Leu Gly
 1               5                  10                  15

<210> SEQ ID NO 6
<211> LENGTH: 14
<212> TYPE: PRT
<213> ORGANISM: artificial
```

```
<220> FEATURE:
<221> NAME/KEY:
<222> LOCATION: 1..14
<223> OTHER INFORMATION: chemically synthesized peptide corresponding to
      amino acids 16-29 of SEQ ID NO. 2

<400> SEQUENCE: 6

Gln Leu Ser Ala Arg Lys Leu Leu Gln Asp Ile Met Ser Arg
 1               5                  10
```